(12) United States Patent
Martinez et al.

(10) Patent No.: US 6,395,266 B1
(45) Date of Patent: *May 28, 2002

(54) TERMINALLY-BRANCHED POLYMERIC LINKERS AND POLYMERIC CONJUGATES CONTAINING THE SAME

(75) Inventors: Anthony J. Martinez, Hamilton Square, NJ (US); Annapurna Pendri, Middletown, CT (US); Richard B. Greenwald, Somerset; Yun H. Choe, Piscataway, both of NJ (US)

(73) Assignee: Enzon, Inc., Piscataway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/293,624

(22) Filed: Apr. 16, 1999

Related U.S. Application Data

(63) Continuation-in-part of application No. 09/062,305, filed on Apr. 17, 1998, now Pat. No. 6,153,655.

(51) Int. Cl.[7] .................. A61K 31/785; A61K 47/30; A61K 31/44; A61K 31/21
(52) U.S. Cl. .................. 424/78.3; 514/772.3; 514/283; 514/506; 514/513; 514/515
(58) Field of Search ................ 514/772.3, 283, 514/506, 513, 515, 613, 626; 424/78.3

(56) References Cited

U.S. PATENT DOCUMENTS

| | | | |
|---|---|---|---|
| 4,179,337 A | 12/1979 | Davis et al. ............... 435/181 |
| 4,943,579 A | 7/1990 | Vishnuvajjala et al. ...... 514/283 |
| 5,183,660 A | 2/1993 | Ikeda et al. ............... 424/94.3 |
| 5,283,339 A | 2/1994 | Arnold et al. .............. 548/104 |
| 5,433,886 A | 7/1995 | Sherbondy et al. ......... 252/180 |
| 5,454,954 A | 10/1995 | Alfano et al. .............. 210/700 |
| 5,489,589 A | 2/1996 | Wittman et al. .......... 514/232.8 |
| 5,498,729 A | 3/1996 | Domb ....................... 548/500 |
| 5,547,981 A | 8/1996 | Greenwald et al. .......... 514/449 |
| 5,569,720 A | 10/1996 | Mongelli et al. .......... 525/329.4 |
| 5,583,206 A | 12/1996 | Snow et al. ................... 534/16 |
| 5,614,549 A | 3/1997 | Greenwald et al. .......... 514/449 |
| 5,622,986 A | 4/1997 | Greenwald et al. .......... 514/449 |
| 5,643,575 A | 7/1997 | Martinez et al. ........... 424/194.1 |
| 5,646,159 A | 7/1997 | Wall et al. ................... 514/279 |
| 5,679,852 A | 10/1997 | Platzek et al. ............... 564/138 |
| 5,693,310 A | 12/1997 | Gries et al. ............... 424/9.365 |
| 5,756,825 A | 5/1998 | Safavy et al. ................ 560/169 |
| 5,885,548 A | 3/1999 | Maier et al. ................ 424/1.65 |
| 5,994,517 A | 11/1999 | Ts'o et al. | |
| 6,020,373 A | 2/2000 | Schellenberg et al. | |
| 6,039,931 A | 3/2000 | Schmitt-Willich et al. | |

FOREIGN PATENT DOCUMENTS

| | | |
|---|---|---|
| WO | WO 81/01145 | 4/1981 |
| WO | WO 93/24476 | 12/1993 |
| WO | WO 95/10304 | 4/1995 |
| WO | WO 96/23794 | 8/1996 |
| WO | WO 99/45964 | 9/1999 |

OTHER PUBLICATIONS

Charlish, Peter. Improved Drug Targeting Polymer Therapeutics Pharmaprojects, Jan 96, pp. 16–18.

Greenwald, R. B., Review Oncalogic, Endocrine & Metabolic Drug Delivery Systems: anticancer prodrug and their polymeric conjugates. Exp. Opin. Ther. Patents (1997) 7(6): 601–609.

Cerny, L. C., et al. A Potential Blood Substitued From A Tetronic Polyol And A Modifid Hemoglob Biomat, Art. Cells & Immob. Biotech., 20(1), 71–93 (1992).

Bogdanov, Alexi A. Jr., et al Long–Circulating Blood Pool Imaging Agents Advanced Drug Delivery Reviews 16 (1995) 335–348.

Ohya, J., et al. Bioactive and Compatible Polymers vol. 10 Jan., 1995, 51–66.

Shearwater Polymers, Inc. catalog Polyethylene Glycol Derivatives 1997–1998.

Williams, Matthew A., and Henry Rapoport, Synthesis of Enantiomerically Pure Diethyletriaminepentaacetic Acid Analogues J. Org. Chem 1193, 58, 1151–1158.

Zalipsky, S., C. Gilon and A. Zilkha, Attachment of Drugs to Polyethylene Glycols Eur. Polym. J vol. 19, No. 12, pp. 1177–1183, 1983.

Weiner, Ben–Zoin and Albert Zilkha, Polyethylene Glycol Derivatives of Procaine J. Med. Chem (1973) vol. 16, No. 5, 573–574.

Shearwater Polymers, Inc. Quarterly Newsletter Mar. 1998.

Greenwald, R. B., et al. Highly Waater Soluble Taxol Derivatives 2'-Polythleneglycol Esters As Potential Prodrugs, Bioorganic & Medical Chemistry Letters, vol. 4 No. 20, pp. 2465–2470, 199.

Ouchi, T., et al. Synthesis And Antitumor Activity of Poly-(Ethylene Glycol)s Linked to 5–Fluorouracil Via A Urethane or Urea Bond. Drug Design & Discovery, 1992, vol. 9, pp. 93–105.

Ueda, Y., et al. Synthesis and Antiumor Evaluation of 2–Oxcarbonylpaclitaxels.

Bioorganic & Medical Chemistry Letters, vol. 4, No. 15. pp. 1861–1864, (1994).

Duncan, Ruth. Drug–Polymer Conjugates: Potential for Improved Chemotherapy Anti–Cancer Drugs 3. pp. 175–210.

Caliceti, P., Preperation and Properties of Monmethoxy Poly(Etholylene Glycol) Doxorubicin Conjug Linked by an Amino Acid or a Peptide As Spacer, IL Framaco, 48(7), 919–932; 1993.

Harris, J. Milton. Laboratory Synthesis of Polyethylene Glycol Derivatives. JMS–Rev. Macromol. Chem. Phys., C25(3), 325–373 (1985).

Ulbrich, Karl. Poly(ethylene glycols)s containing enzymatically degradable bonds. Makromol. Chem. 187, 1131–1144 (1986).

Benaglia, Maurizio. Synthesis of New Poly(ethyleneglycol)s with a High Loading Capacity. J. Org. Chem. 1998, 63, 8628–8629.

Chen, Jiyan. Thiol–Reactive Luminescent Chelates of Terbium and Europium. Bioconjugate Chem. 1999, 10, 311–315.

Hines, Jennifer V., et al. Paramagnetic Oligonucleotides: Contrast Agents for Magnetic Resonance Imaging with Proton Relaxation Enhancement Effects. Bioconjugate Chem., vol. 10, No. 2, 1999, pp 155–158.

King, Dalton H., et al. Monoclonal Antibody Conjugates of Doxorubicin Prepared with Branched Linkers: A Novel Method for Increasing the Potency of Doxorubicin Immunoconjugates. Bioconjugate Chem., vol. 10, 1999, pp 279–288.

Ranganathan, D., et al. Synthesis of Totally Chiral, Multiple Armed, Poly Glu and Poly Asp Scaffoldings on Bifunctional Adamantane Core, Tetrahedron Letters, vol. 38, No. 7, p. 1265–68 (1997).

Twyman, L.J. et al. The Synthesis of Water Soluble Dendrimers, and their Application as Possible Drug Delivery Systems, Tetrahedron Letters, vol. 40, p. 1743–46 (1999).

*Primary Examiner*—Thurman K. Page
*Assistant Examiner*—Blessing M. Fubara
(74) *Attorney, Agent, or Firm*—Roberts & Mercanti, LLP

(57) ABSTRACT

The present invention is directed to polymeric-prodrug transport forms of the formula:

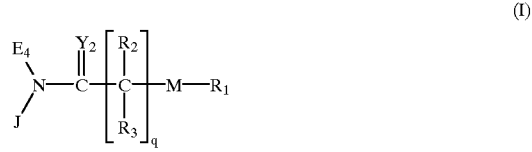

wherein:

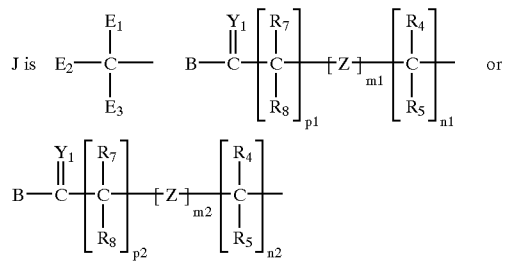

$E_{1-4}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy,

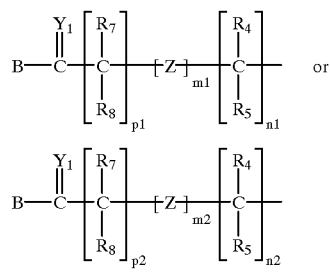

and at least one of $E_{1-4}$ includes a B moiety, wherein B is a leaving group, OH, a residue of a hydroxyl-or amino-containing moiety or

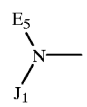

wherein $J_1$ is the same as J, or another member of the group defining J and $E_5$ is the same as $E_{1-4}$, or another member of the group defining $E_{1-4}$;

$Y_{1-2}$ are independently O, S or $NR_9$;

M is a heteroatom selected from either X or Q; wherein X is an electron withdrawing group and Q is a moiety containing a free electron pair positioned three to six atoms from $C(=Y_2)$;

$R_{2-5}$ and $R_{7-9}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-16}$ heteroalkyls, substituted $C_{1-6}$ heteroalkyls, $C_{1-6}$ alkoxy, phenoxy and $C_{1-6}$ heteroalkoxy;

(m1) and (m2) are independently zero or one;

(n1), (n2), (p1), (p2) and (q) are independently zero or a positive integer,

Z is an electron withdrawing group; and $R_1$ is a polymeric residue.

which is optionally capped with a moiety of the formula:

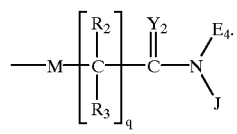

(V)

METHOD A

METHOD B

METHOD A

METHOD B

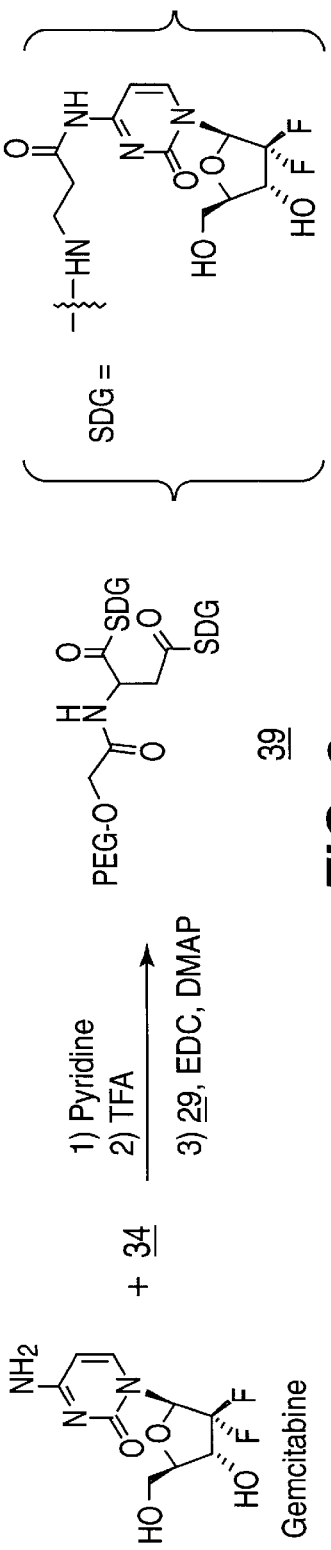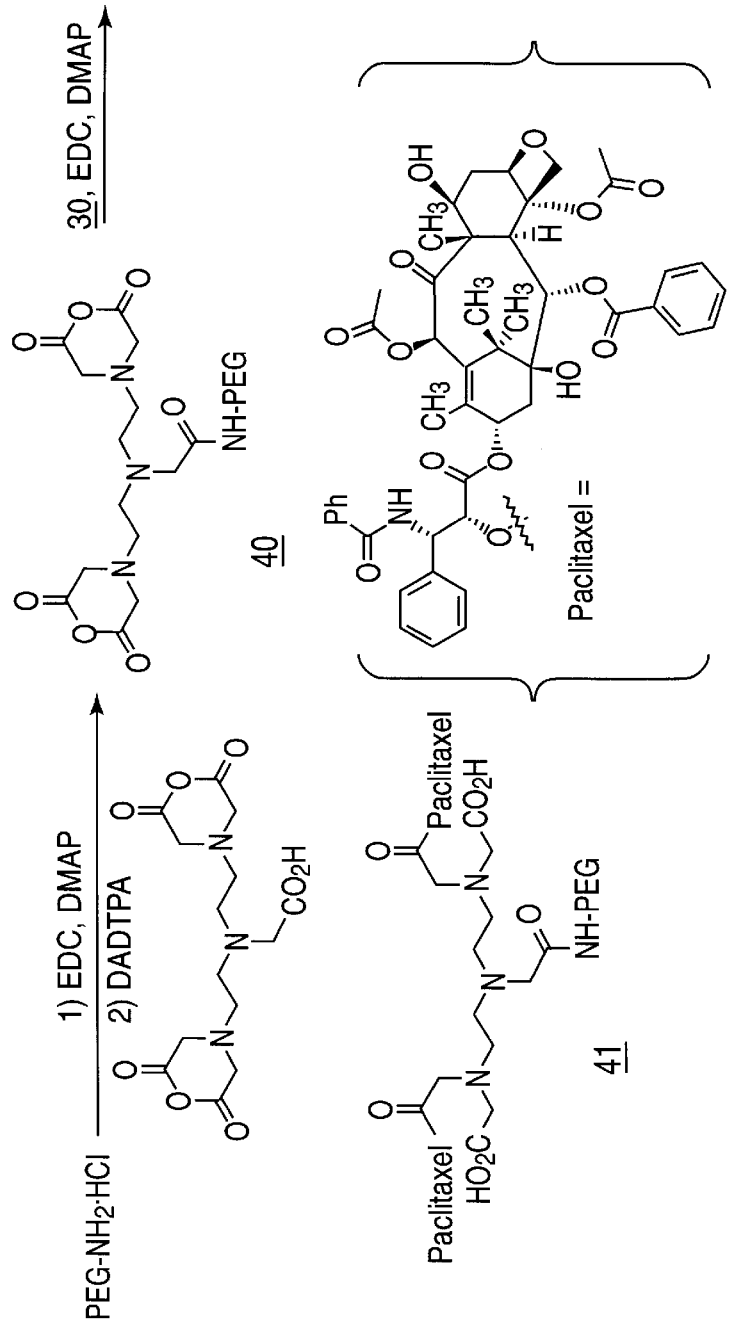
FIG. 8
FIG. 9

TERMINALLY-BRANCHED POLYMERIC LINKERS AND POLYMERIC CONJUGATES CONTAINING THE SAME

CROSS-REFERENCE TO RELATED APPLICATIONS

This application is a continuation-in-part of Ser. No. 09/062,305 filed Apr. 17, 1998 now U.S. Pat. No. 6,153,655 which issued on Nov. 28, 2000, the contents of which are incorporated herein by reference.

TECHNICAL FIELD

The present invention relates to new types of terminally-activated polymeric materials which are useful in forming long-acting conjugates of bioactive materials. In particular, the invention relates to polymeric-based conjugates having increased therapeutic payloads and methods of preparing the same.

BACKGROUND OF THE INVENTION

Over the years, several methods of administering biologically-effective materials to mammals have been proposed. Many medicinal agents are available as water-soluble salts and can be included in pharmaceutical formulations relatively easily. Problems arise when the desired medicinal agent is either insoluble in aqueous fluids or is rapidly degraded in vivo. Alkaloids are often especially difficult to solubilize.

One way to solubilize medicinal agents is to include them as part of a soluble product. Prodrugs include chemical derivatives of a biologically-active parent compound which, upon administration, eventually liberate the parent compound in vivo. Prodrugs allow the artisan to modify the onset and/or duration of action of an agent in vivo and can modify the transportation, distribution or solubility of a drug in the body. Furthermore, prodrug formulations often reduce the toxicity and/or otherwise overcome difficulties encountered when administering pharmaceutical preparations. Typical examples of prodrugs include organic phosphates or esters of alcohols or thioalcohols. See *Remington's Pharmaceutical Sciences*, 16the Ed., A. Osol, Ed. (1980), the disclosure of which is incorporated by reference herein.

Prodrugs are often biologically inert or substantially inactive forms of the parent or active compound. The rate of release of the active drug, i.e. the rate of hydrolysis, is influenced by several factors but especially by the type of bond joining the parent drug to the modifier. Care must be taken to avoid preparing prodrugs which are eliminated through the kidney or reticular endothelial system, etc. before a sufficient amount of hydrolysis of the parent compound occurs.

Incorporating a polymer as part of a prodrug system has been suggested to increase the circulating life of a drug. However, it has been determined that when only one or two polymers of less than about 10,000 daltons each are conjugated to certain biologically active substances such as alkaloid compounds, the resulting conjugates are rapidly eliminated in vivo, especially if a somewhat hydrolysis-resistant linkage is used. In fact, such conjugates are so rapidly cleared from the body that even if a hydrolysis-prone ester linkage is used, not enough of the parent molecule is regenerated in vivo to be therapeutic.

Camptothecin and related biologically active analogs are often poorly water soluble and are examples of substances which would benefit from PEG prodrug technology. A brief overview of some previous work in the field is presented below.

Ohya, et al., J. *Bioactive and Compatible Polymers* Vol. Jan. 10, 1995, 51–66, disclose doxorubicin-PEG conjugates which are prepared by linking the two substituents via various linkages including esters. The molecular weight of the PEG used, however, is only about 5,000 at most. Thus, the in vivo benefits are not fully realized because the conjugates are substantially excreted prior to sufficient linkage hydrolysis.

U.S. Pat. No. 4,943,579 discloses certain simple 20(S)-camptothecin amino acid esters in their salt forms as water soluble prodrugs. The reference does not, however, disclose using an amino acid as part of a linkage which would attach the alkaloid to a relatively high molecular weight polymer in order to form a prodrug. As evidenced by the data provided in Table 2 of the '579 patent, hydrolysis is rapid. Consequently, at physiologic pH, the insoluble base is rapidly generated after injection, binds to proteins and is quickly eliminated from the body before a therapeutic effect can be achieved. A related effort was directed to developing a water-soluble camptothecin sodium salt. Unfortunately, the water-soluble sodium salt of camptothecin remained too toxic for clinical application (Gottlieb et al,. 1970 *Cancer Chemother, Rep.* 54, 461; Moertel et al,. 1972 *ibid,* 56, 95; Gottlieb et al., 1972 *ibid,* 56, 103).

Commonly-assigned PCT publication WO 96/23794 describes bis-conjugates in which one equivalent of the hydroxyl-containing drug is attached to each terminal of the polymer. In spite of this advance, techniques which would further increase the payload of the polymer have been sought.

Thus, there continues to be a need to provide additional technologies for forming prodrugs of therapeutic moieties such as camptothecin and related analogs. The present invention addresses this need.

SUMMARY OF THE INVENTION

In one aspect of the invention, compounds of Formula (I) are provided:

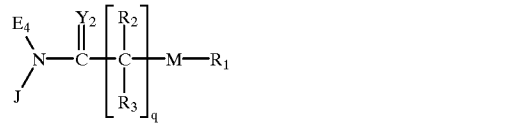

wherein:

J is

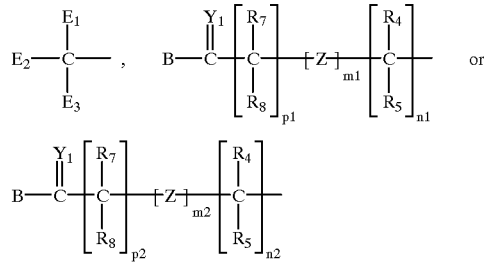

$E_{1-4}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy,

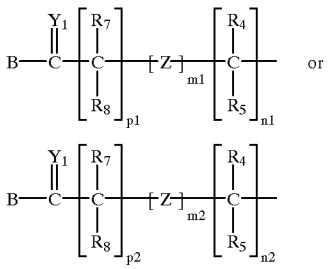

and at least one of $E_{1-4}$ includes a B moiety, wherein B is a leaving group, OH, a residue of a hydroxyl- or amine-containing moiety or

wherein $J_1$ is the same as J, or another member of the group defining J and $E_5$ is the same as $E_{1-4}$, or another member of the group defining $E_{1-4}$;

$Y_{1-2}$ are independently O or S;

M is a heteroatom selected from either X or Q; wherein X is an electron withdrawing group and Q is a moiety containing a free electron pair positioned three to six atoms from $C(=Y_2)$;

$R_{2-5}$ and $R_{7-8}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroakoxy;

(m1) and (m2) are independently zero or one;

(n1), (n2), (p1), (p2) and (q) are independently zero or a positive integer;

Z is an electron withdrawing group; and $R_1$ is a polymeric residue such as a water-soluble polyalkylene oxide, preferably having a molecular weight of at least about 20,000 Daltons.

In preferred aspects of the invention, the polymeric residue is also substituted on the distal portion with another branching group to provide compounds of the formula (I'):

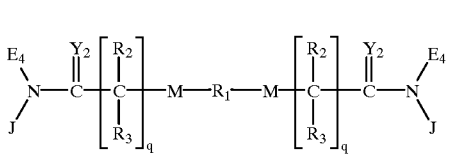

(I')

where all variables are as previously defined. The bifunctional compounds are thus formed when the polymeric residue ($R_1$) includes both an alpha and an omega terminal linking group so that two, four or more equivalents of a biologically active agent, drug or protein, designated herein as B, can be delivered. Multifunctional compounds represented by the formula (I') are preferred.

When B is a residue of a hydroxyl-containing moiety or an amine-containing moiety, each B is attached via a hydrolyzable linkage which attaches to the polymer residue terminus.

Examples of hydroxyl-containing moieties for which on or more of improved aqueous solubility, decreased antigenicity, prodrug and/or controlled release delivery is desired include chemotherapeutic compound residues such as anti-fungal compounds, including triazoles, echinocandins, pneumocandins, etc, anti-cancer compounds such as camptothecin, paclitaxel, etoposide, anti-cancer platinum compounds containing OH groups, floxuridine or podophyllotoxin. In still further embodiments, other oncolytic agents, non-oncolytic agents such as anti-inflammatory agents, including steroidal compounds, as well as therapeutic low molecular weight peptides such as insulin are also contemplated.

Examples of amine-containing moieties for which one or more of improved aqueous solubility, decreased antigenicity, prodrug and/or controlled release delivery is desired include antimetabolites such as Ara-C or gemcitabine.

Alternatively, B can be a leaving group such as N-hydroxybenzotriazolyl, N-hydroxyphthalimidyl, halogen, p-nitrophenoxy, imidazolyl, N-hydroxysuccinimidyl, thiazolidyl thione, or other activating groups.

For purposes of the present invention, the term "residue" shall be understood to mean that portion of a biologically active compound which remains after the biologically active compound has undergone a substitution reaction in which the prodrug carrier portion has been attached.

For purposes of the present invention, the term "alkyl" shall be understood to include straight, branched, substituted, e.g. halo-, alkoxy-, and nitro- $C_{1-12}$ alkyls, $C_{3-8}$ cycloalkyls or substituted cycloalkyls, etc.

For purposes of the present invention, the term "substituted" shall be understood to include adding or replacing one or more atoms contained within a functional group or compound with one or more different atoms.

The term "sufficient amounts" for purposes of the present invention shall mean an amount which achieves a therapeutic effect as such effect is understood by those of ordinary skill in the art.

One of the chief advantages of the compounds of the present invention is that the prodrugs have a higher payload per unit of polymer than previous techniques. Another advantage is that the linkers achieve a proper balance between the rate of parent drug-polymer linkage hydrolysis and the rate of clearance of prodrug from the body. The linkages between the polymer and the parent compounds, also referred to herein as biologically-active nucleophiles, hydrolyze at a rate which allows a sufficient amount of the parent molecules to be released in vitro before clearance of the prodrug from the plasma or body. The high payload polymeric conjugates of the present invention are thus unique delivery systems which can contain up to four or a greater number of molecules of a drug.

Methods of making and using the compounds and conjugates described herein are also provided.

BRIEF DESCRIPTION OF THE DRAWINGS

FIGS. 3–9 schematically illustrate compounds synthesized in the Examples.

DETAILED DESCRIPTION OF THE INVENTION

A. THE PRODRUGS

Figure 1A:
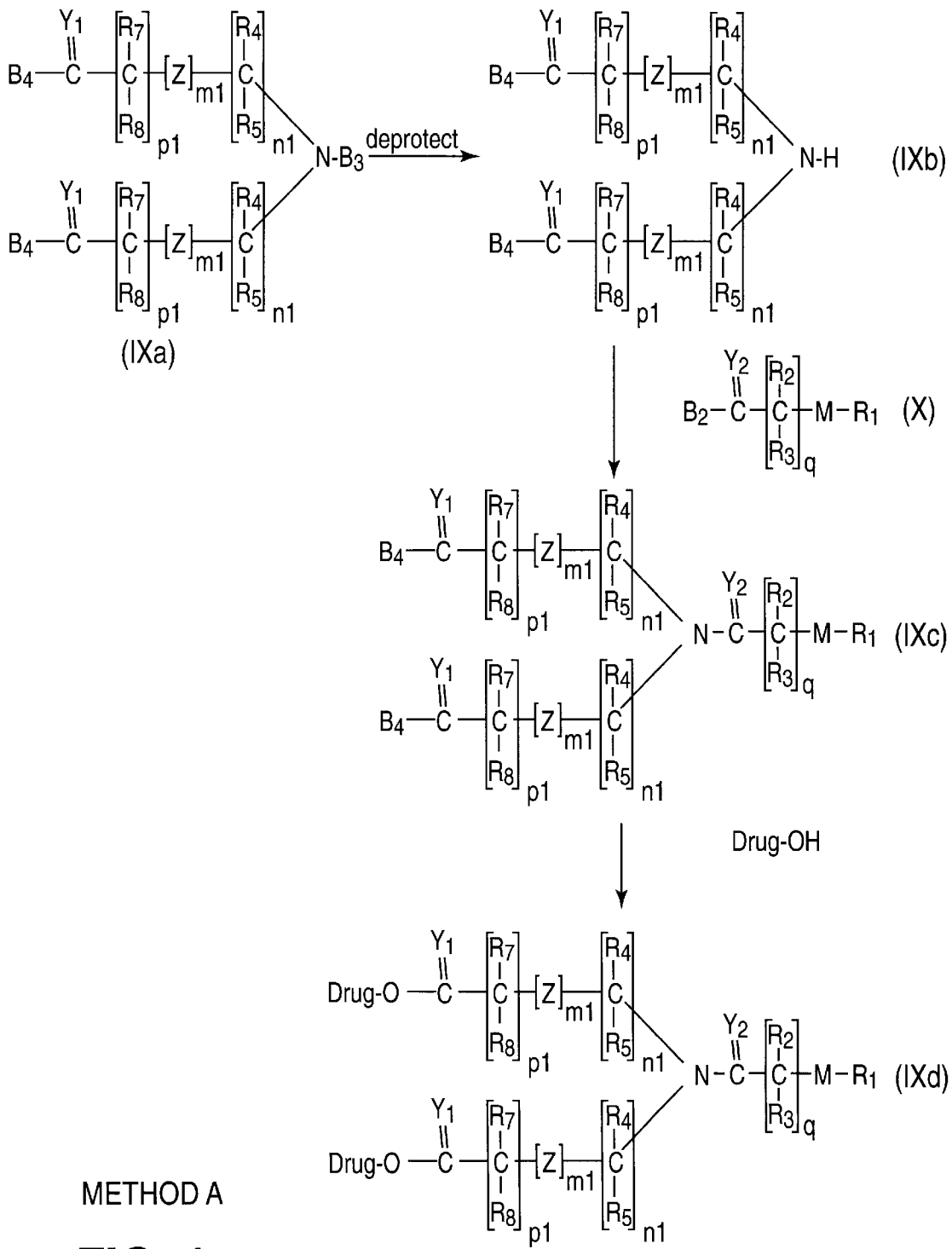
FIGS. 1a, 1b, 2a, 2b schematically illustrate methods of forming compounds of the present invention.

In one preferred embodiment of the invention, the compositions of the invention comprise the formula:

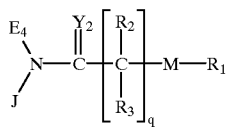
(I)

wherein:

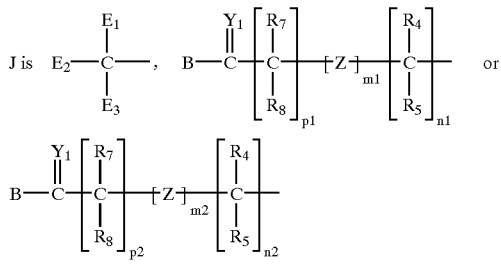

$E_{1-4}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy,

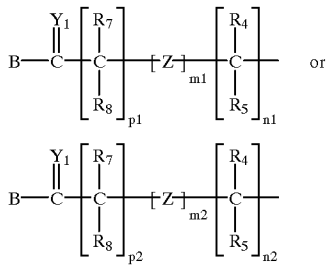

and at least one of $E_{1-4}$ includes a B moiety, wherein B is a leaving group, OH, a residue of a hydroxyl-or amine-containing moiety or

wherein $J_1$ is the same as J, or another member of the group defining J; optionally when $J_1$ is the same as J, m1,n1 and p1, etc. are different from those used in J; and $E_5$ is the same as $E_{1-4}$, or another member of the group defining $E_{1-4}$;

$Y_{1-2}$ are independently O or S;

M is a heteroatom selected from either X or Q; wherein X is an electron withdrawing group and Q is a moiety containing a free electron pair positioned three to six atoms from $C(=Y_2)$;

$R_{2-5}$ and $R_{7-8}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroakoxy;

(m1) and (m2) are independently zero or one;

(n1), (n2), (p1), (p2) and (q) are independently zero or a positive integer;

Z is an electron withdrawing group; and $R_1$ is a polymeric residue.

Preferably, the polymer residue portion, designated $R_1$ herein, is further substituted with a terminal capping moiety ($A_1$) which is distal to the linker portion containing the branched amine. A non-limiting list of suitable capping groups includes hydrogen, $CO_2H$, $C_{1-6}$ alkyl moieties, biologically active and inactive moieties, dialkyl acyl urea alkyls, and moieties of Formula (V):

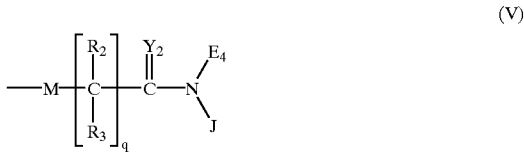
(V)

wherein all variables are as defined above.

Within Formula (I), $Y_1$ and $Y_2$ are preferably oxygen, $R_{2-5}$ are preferably H or methyl, (n) is 1 or 2, (p) is 1 and (q) is 1.

In those aspects of this embodiment where bis-substituted polymeric residues are desired, some preferred polymeric transport systems of the invention are shown below:

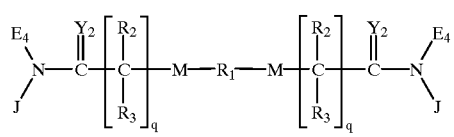

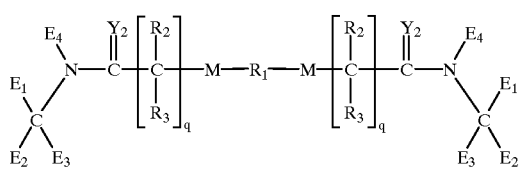

-continued

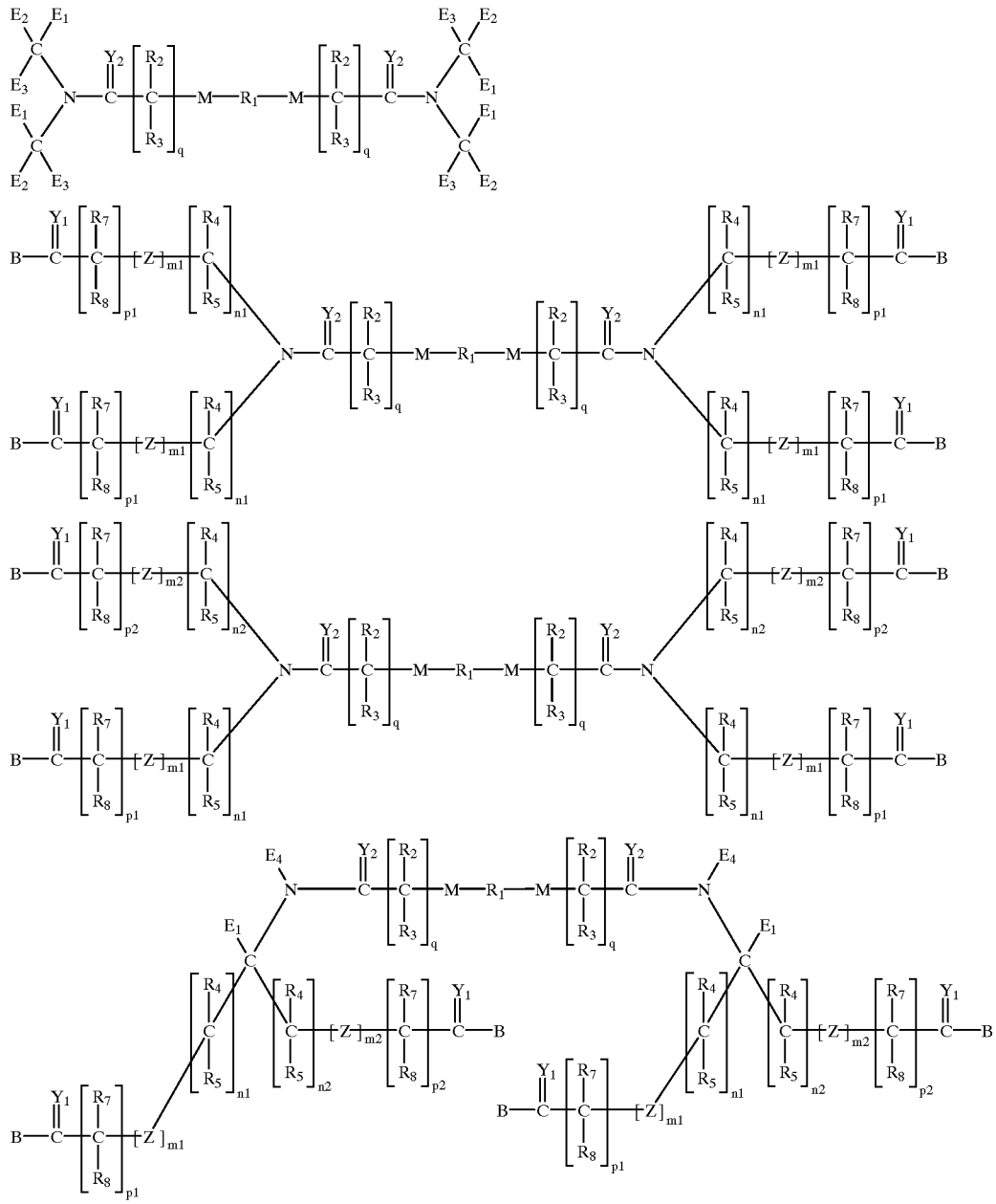

where all variables are as previously defined.

B. THE PRODRUG LINKAGE

1. The Electron Withdrawing Groups X and Z

Within the Formula (I), X and Z are variables which represent electron withdrawing groups. In particular, X and Z can be independently selected from moieties such as O, S, SO, $SO_2$, $C(=Y_3)$ wherein $Y_3$ is either O or S, and $NR_6$ wherein $R_6$ is one of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls, branched alkyls, aryls, substituted aryls, $C_{1-6}$ alkyl aralkyls, heteroalkyls, substituted heteroalkyls or substituted $C_{1-6}$ alkyls such as carboxyalkyls, aminoalkyls, dialkylaminos, hydroxyalkyls or mercaptoalkyls, to name but a few. Preferably, X is either O or $NR_6$ and $R_6$ is preferably H. In preferred embodiments, when X is oxygen, the oxygen is provided as the terminal portion of the PEG polymer. The terminal oxygen can be substituted to provide the other X moieties described herein using techniques apparent to those of ordinary skill without undue experimentation.

2. Portion of the Linker

When M is Q, the polymer, $R_1$, is preferably attached to Q via a heteroatom such as oxygen. Q is a moiety containing a free electron pair positioned three to six atoms from the $C(=Y_2)$ moiety. In a preferred embodiment, the free electron pair is five atoms from the $C(=Y_2)$. Q can be selected from the non-limiting list of cycloalkyls, aryls, aralkyl groups substituted with O, S or $NR_9$, where $R_9$ is one of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls; —$CH_2$—$C(=O)$—NH—, and ortho-substituted phenyls such as

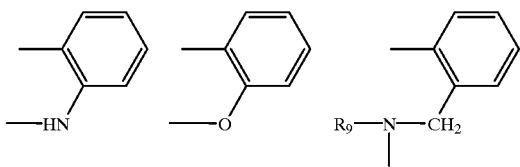

Preferably, $R_9$ is H, a $C_{1-6}$ alkyl or substituted $C_{1-6}$ alkyl. The free electron pair can be anywhere along the Q moiety as long as the defined spacing between the free electron pair and the oxygen is maintained. In these embodiments, $R_1$ is attached to Q via $NR_9$, O, or S. Thus, Q assists hydrolysis of the prodrug linkage by anchimeric assistance because the free electron pair moiety can generate a three- to six-membered, but preferably five-membered, ring by-product upon hydrolysis of the preferably ester linkage.

3. Drug Generation Via Hydrolysis of the Prodrug

The prodrug compounds of the present invention are designed so that the $t_{1/2}$ of hydrolysis is <$t_{1/2}$ elimination in plasma.

The linkages included in the compounds have hydrolysis rates in the plasma of the mammal being treated which is short enough to allow sufficient amounts of the parent compounds, i.e. the amino- or hydroxyl-containing bioactive compound, to be released prior to elimination. Some preferred compounds of the present invention, i.e. those in which (n) is 1, have a $t_{1/2}$ for hydrolysis in plasma ranging from about 5 minutes to about 12 hours. Preferably, the compositions have a plasma $t_{1/2}$ hydrolysis ranging from about 0.5 to about 8 hours and most preferably from about 1 to about 6 hours.

C. SUBSTANTIALLY NON-ANTIGENIC POLYMERS

As stated above, $R_1$ is a polymeric residue which is preferably substantially non-antigenic. In preferred aspects of the invention, $R_1$ further includes a capping group A which can be hydrogen, $CO_2H$, $C_{1-6}$ alkyl moieties, carboxyalkyl, dialkyl acyl urea alkyls, or a compound of formula (V) shown below which forms a bis-system:

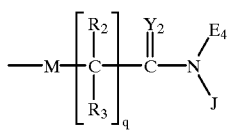

(V)

wherein all variables are the same as defined above. Suitable examples of such polymers include polyalkylene oxides such as polyethylene glycols. The general formula for PEG and its derivatives, i.e.

where (x) represents the degree of polymerization (i.e. from about 10 to about 2,300) or number of repeating units in the polymer chain and is dependent on the molecular weight of the polymer, (n3) is zero or a positive integer, ($A_2$) is a capping group as defined herein, i.e. an, amino, carboxy, halo, $C_{1-6}$ alkyl or other activating group and ($A'_2$) is the same as ($A_2$) or another ($A_2$) moiety. Also useful are polypropylene glycols, branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998". The disclosure of each of the foregoing is incorporated herein by reference. It will be understood that the water-soluble polymer can be functionalized for attachment to the linkage via M, X or Q herein. As an example, the PEG portion of the inventive compositions can be one of the following non-limiting compounds:

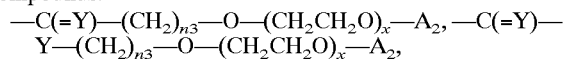

and

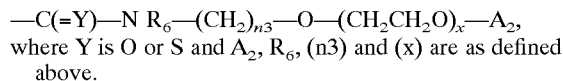

where Y is O or S and $A_2$, $R_6$, (n3) and (x) are as defined above.

In many aspects of the present invention, bis-activated polyethylene glycols are preferred when di-substituted polymer conjugates are desired. Alternatively, polyethylene glycols (PEG's), mono-activated, $C_{1-4}$ alkyl-terminated PAO's such as mono-methyl-terminated polyethylene glycols (mPEG's) are preferred when mono-substituted polymers are desired.

In order to provide the desired hydrolyzable linkage, mono- or di-acid activated polymers such as PEG acids or PEG diacids can be used as well as mono- or di-PEG amines and mono- or di-PEG diols. Suitable PAO acids can be synthesized by first converting mPEG-OH to an ethyl ester followed by saponification. See also Gehrhardt, H., et al. Polymer Bulletin 18:487 (1987) and Veronese, F. M., et al., J. Controlled Release 10; 145 (1989). Alternatively, the PAO-acid can be synthesized by converting mPEG-OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in number average molecular weight, polymers ranging from about 2,000 to about 100,000 are usually selected for the purposes of the present invention. Molecular weights of from about 5,000 to about 50,000 are preferred and 20,000 to about 40,000 are particularly preferred. The number average molecular weight of the polymer selected for inclusion in the prodrug must be sufficient so as to provide sufficient circulation of the prodrug before hydrolysis of the linker. Within the ranges provided above, polymers having molecular weight ranges of at least 20,000 are preferred for chemotherapeutic and organic moieties. In the case of some nucleophiles such as certain proteins, enzymes and the like, the number average molecular weight of the polymeric residue can range from about 2,000 to about 20,000.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, hydroxypropylmethacrylamide (HPMA), and copolymers thereof etc. and the like can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" and "substantially non-antigenic" shall be understood to include all polymeric materials understood in the art as being substantially non-toxic and not eliciting an appreciable immune response in mammals.

It will be clear from the foregoing that other polyalkylene oxide derivatives of the foregoing, such as the polypropylene glycol acids, etc., as well as other bi-functional linking groups are also contemplated.

D. PRODRUG CANDIDATES

1. Residues of Hydroxyl-containing Compounds a. Camptothecin and Related Topoisomerase I Inhibitors

Camptothecin is a water-insoluble cytotoxic alkaloid produced by *Camptotheca accuminata* trees indigenous to China and nothapodytes foetida trees indigenous to India. Camptothecin and related compounds and analogs are also known to be potential anticancer or antitumor agents and have been shown to exhibit these activities in vitro and in vivo. Camptothecin and related compounds are also candidates for conversion to the prodrugs of the present invention. Camptothecin and certain related analogues share the structure:

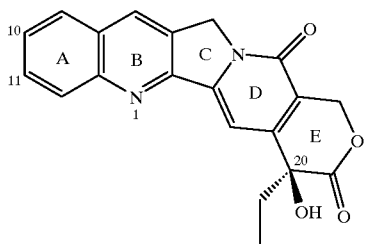

From this core structure, several known analogs have been prepared. For example, the A ring in either or both of the 10- and 11-positions can be substituted with an OH. The A ring can also be substituted in the 9-position with a straight or branched $C_{1-30}$ alkyl or $C_{1-17}$ alkoxy, optionally linked to the ring by a heteroatom i.e.- O or S. The B ring can be substituted in the 7-position with a straight or branched $C_{1-30}$ alkyl or substituted alkyl-, $C_{5-8}$ cycloakyl, $C_{1-30}$ (alkoxy, phenyl alkyl, etc., alkyl carbamate, alkyl carbazides, phenyl hydrazine derivatives, amino-, aminoalkyl-, aralkyl, etc. Other substitutions are possible in the C, D and E rings. See, for example, U.S. Pat. Nos. 5,004,758; 4,943,579; Re 32,518, the contents of which are incorporated herein by reference. Such derivatives can be made using known synthetic techniques without undue experimentation. Preferred camptothecin derivatives for use herein include those which include a 20—OH or another OH moiety which is capable of reacting directly with activated forms of the polymer transport systems described herein or to the linking moiety intermediates, e.g. iminodiacetic acid, etc., which are then attached to a polymer such as PEG. Reference to camptothecin analogs herein has been made for purposes of illustration and not limitation.

b. Taxanes and Paclitaxel Derivatives

One class of compounds included in the prodrug compositions of the present invention is taxanes. For purposes of the present invention, the term "taxane" includes all compounds within the taxane family of terpenes. Thus, taxol (paclitaxel), 3'-substituted tert-butoxy-carbonyl-amine derivatives (taxoteres) and the like as well as other analogs which are readily synthesized using standard organic techniques or are available from commercial sources such as Sigma Chemical of St. Louis, Mo. are within the scope of the present invention. Representative taxanes are shown below.

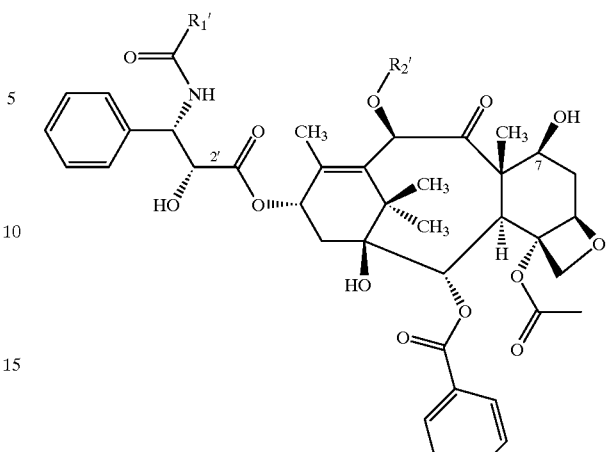

Paclitaxel: $R_1' = C_6H_5$———, $R_2' = CH_3C(=O)$
Taxotere: $R_1' = (CH_3)_3C(=O)$———, $R_2' = H$ These derivatives have been found to be effective anticancer agents. Numerous studies indicate that the agents have activity against several malignancies. To date, their use has been severely limited by, among other things, their short supply, poor water solubility and a tendency to cause hypersensitivity. It is to be understood that other taxanes including the 7-aryl-carbamates and 7-carbazates disclosed in commonly assigned U.S. Pat. Nos. 5,622,986 and 5,547,981 can also be included in the prodrugs of the present invention. The contents of the foregoing U.S. patents are incorporated herein by reference. The only limitation on the taxane is that it must be capable of undergoing a hydroxyl based substitution reaction such as at the 2' position. Paclitaxel, however, is a preferred taxane.

c. Additional Biologically-Active Moieties

In addition to the foregoing molecules, the prodrug formulations of the present invention can be prepared using many other compounds. For example, biologically-active compounds such as bis-PEG conjugates derived from compounds such as gemcitabine:

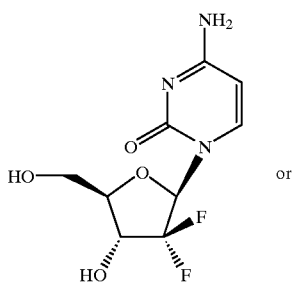

or podophyllotoxin:

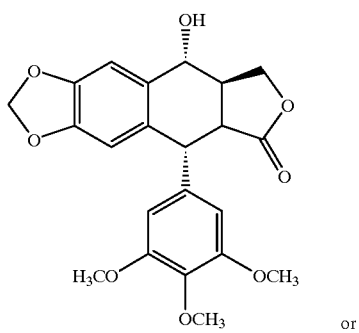

or triazole-based antifungal agents such as fluconazole:

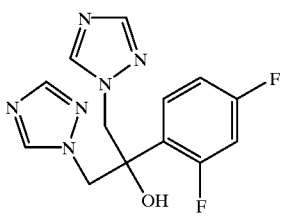

or ciclopirox:

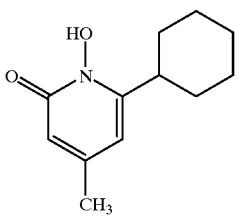

or Ara-C:

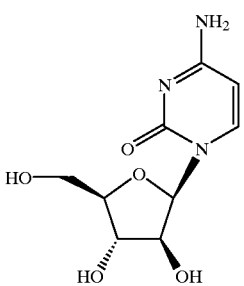

The parent compounds selected for prodrug forms need not be substantially water-insoluble, although the polymer-based prodrugs of the present invention are especially well suited for delivering such water-insoluble compounds. Other useful parent compounds include, for example, certain low molecular weight biologically active proteins, enzymes and peptides, including peptido glycans, as well as other anti-tumor agents; cardiovascular agents such as forskolin; anti-neoplastics such as combretastatin, vinblastine, doxorubicin, maytansine, etc.; anti-infectives such as vancomycin, erythromycin, etc.; anti-fungals such as nystatin, amphotericin B, triazoles, papulocandins, pneumocandins, echinocandins, polyoxins, nikkomycins, pradimicins, benanomicins, etc. see, "Antibiotics That Inhibit Fungal Cell Wall Development" *Annu. Rev. Microbiol.* 1994, 48:471–97, the contents of which are incorporated herein by reference; anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like.

The foregoing is illustrative of the biologically active moieties which are suitable for the prodrugs of the present invention. It is to be understood that those biologically active materials not specifically mentioned but having suitable ester-forming groups, i.e. hydroxyl moieties, are also intended and are within the scope of the present invention. It is also to be understood that the prodrug conjugates of the present invention may also include minor amounts of compounds containing not only one equivalent of drug and polymer but also a moiety which does not effect bioactivity in vivo. For example, it has been found that in some instances, in spite of reacting diacids with drug molecules having a single linkage point, the reaction conditions do not provide quantitative amounts of prodrugs with two equivalents of drug per polymer. By-products of the reactants can sometimes be formed such as acyl ureas if carbodiimides are used.

2. Residues of Amine-containing Compounds

In some aspects of the invention, B is a residue of an amine-containing compound, a non-limiting list of such suitable compounds include residues of organic compounds, enzymes, proteins, polypeptides, etc. Organic compounds include, without limitations moieties such as anthracycline compounds including daunorubicin, doxorubicin; ρ-aminoaniline mustard, melphalan, Ara-C (cytosine arabinoside) and related anti-metabolite compounds, e.g., gemcitabine, etc. Alternatively, B can be a residue of an amine-containing cardiovascular agent, anti-neoplastic, anti-infective, anti-fungal such as nystatin and amphotericin B, anti-anxiety agent, gastrointestinal agent, central nervous system-activating agent, analgesic, fertility agent, contraceptive agent, anti-inflammatory agent, steroidal agent, anti-urecemic agent, vasodilating agent, vasoconstricting agent, etc.

In a preferred aspect of the invention, the amino-containing compound is a biologically active compound that is suitable for medicinal or diagnostic use in the treatment of animals, e.g., mammals, including humans, for conditions for which such treatment is desired. The foregoing list is meant to be illustrative and not limiting for the compounds which can be modified. Those of ordinary skill will realize that other such compounds can be similarly modified without undue experimentation. It is to be understood that those biologically active materials not specifically mentioned but having suitable amino-groups are also intended and are within the scope of the present invention.

The only limitations on the types of amino-containing molecules suitable for inclusion herein is that there is available at least one (primary or secondary) amine-containing position which can react and link with a carrier portion and that there is not substantial loss of bioactivity after the prodrug system releases and regenerates the parent compound.

It is noted that parent compounds suitable for incorporation into the prodrug compositions of the invention, may themselves be substances/compounds which are not active after hydrolytic release from the linked composition, but which will become active after undergoing a further chemical process/reaction. For example, an anticancer drug that is delivered to the bloodstream by the double prodrug transport system, may remain inactive until entering a cancel or tumor cell, whereupon it is activated by the cancer or tumor cell chemistry, e.g., by an enzymatic reaction unique to that cell.

E. SYNTHESIS OF THE POLYMERIC PRODRUG TRANSPORT SYSTEM

Figure 1B:
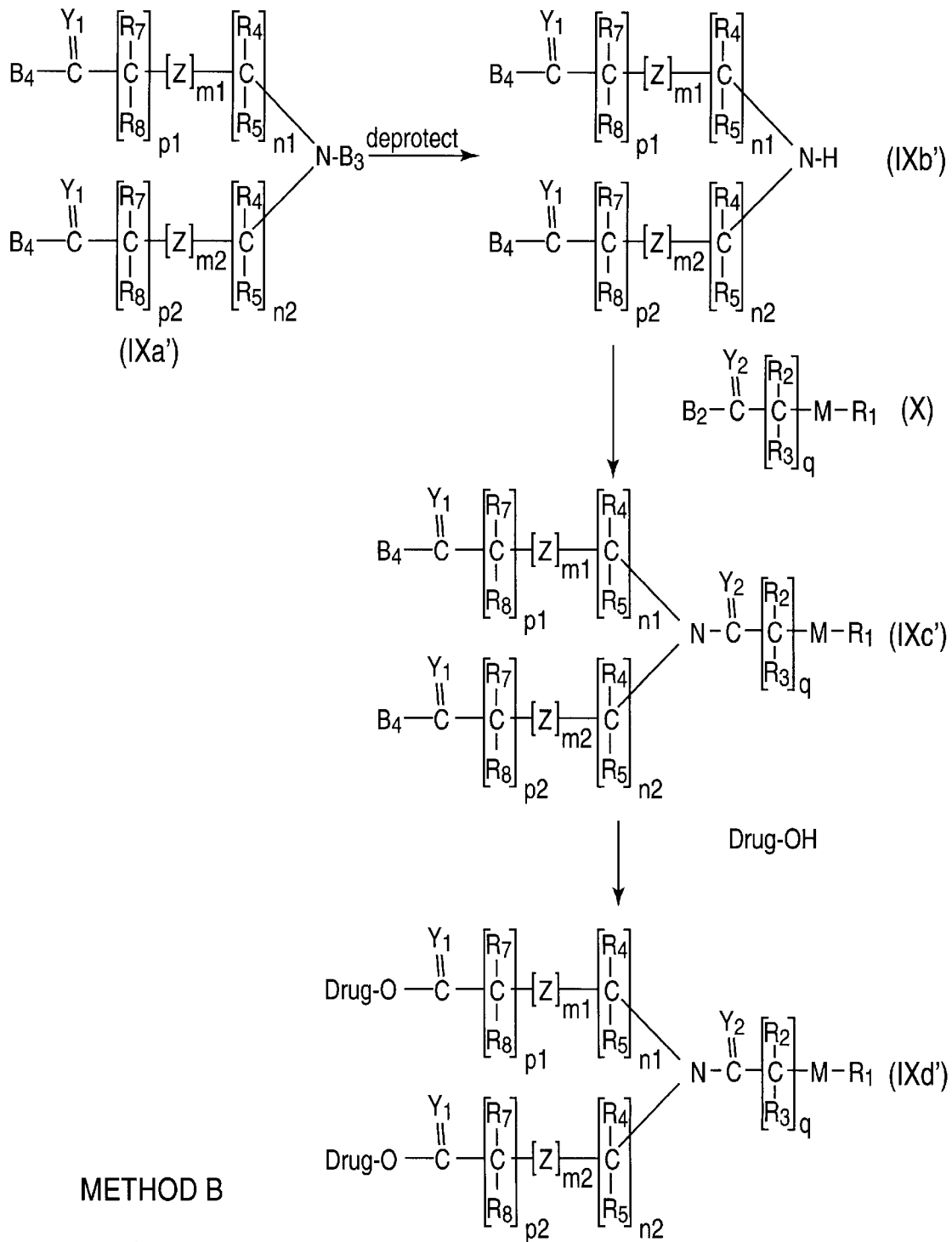
Figure 2A:
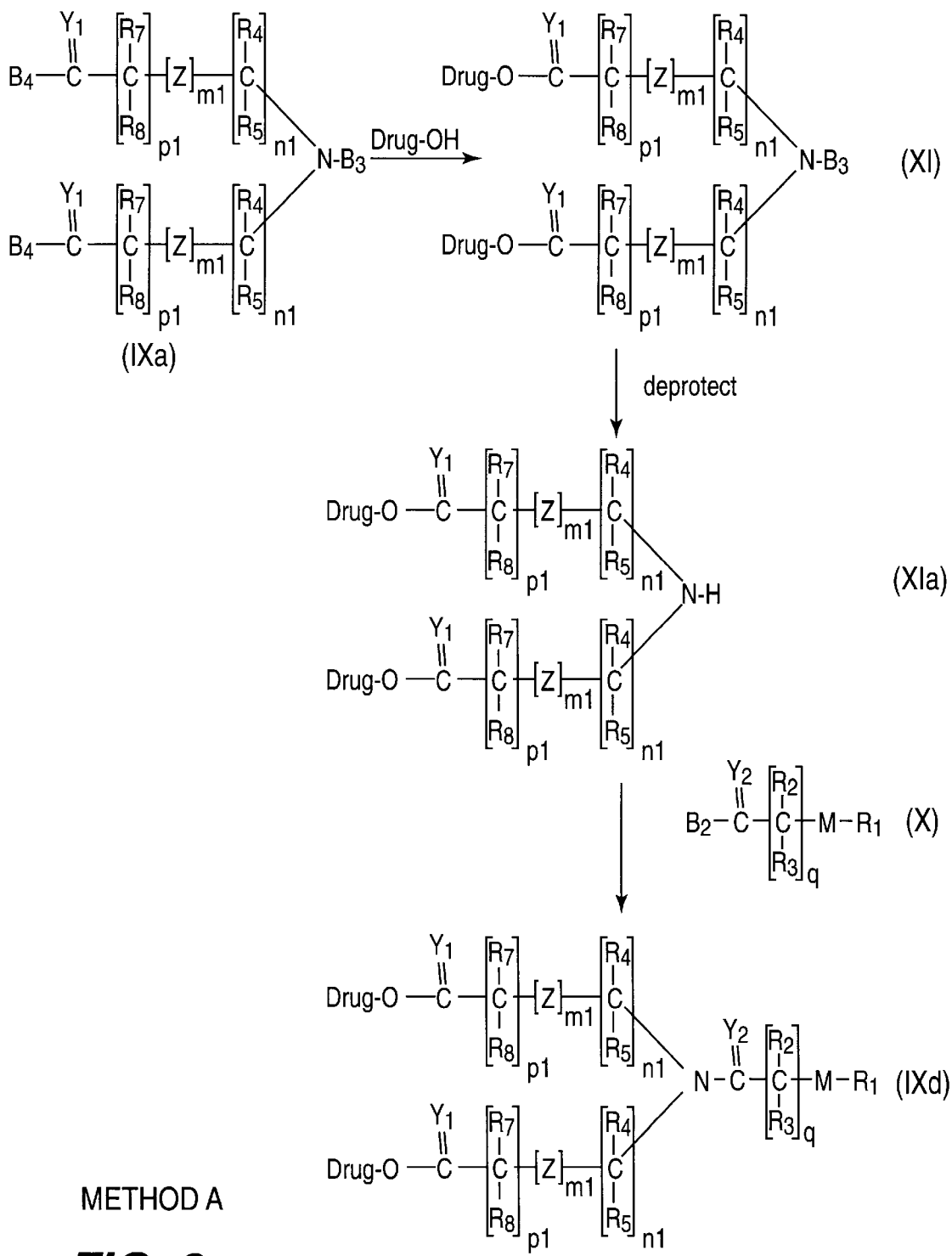
Figure 2B:
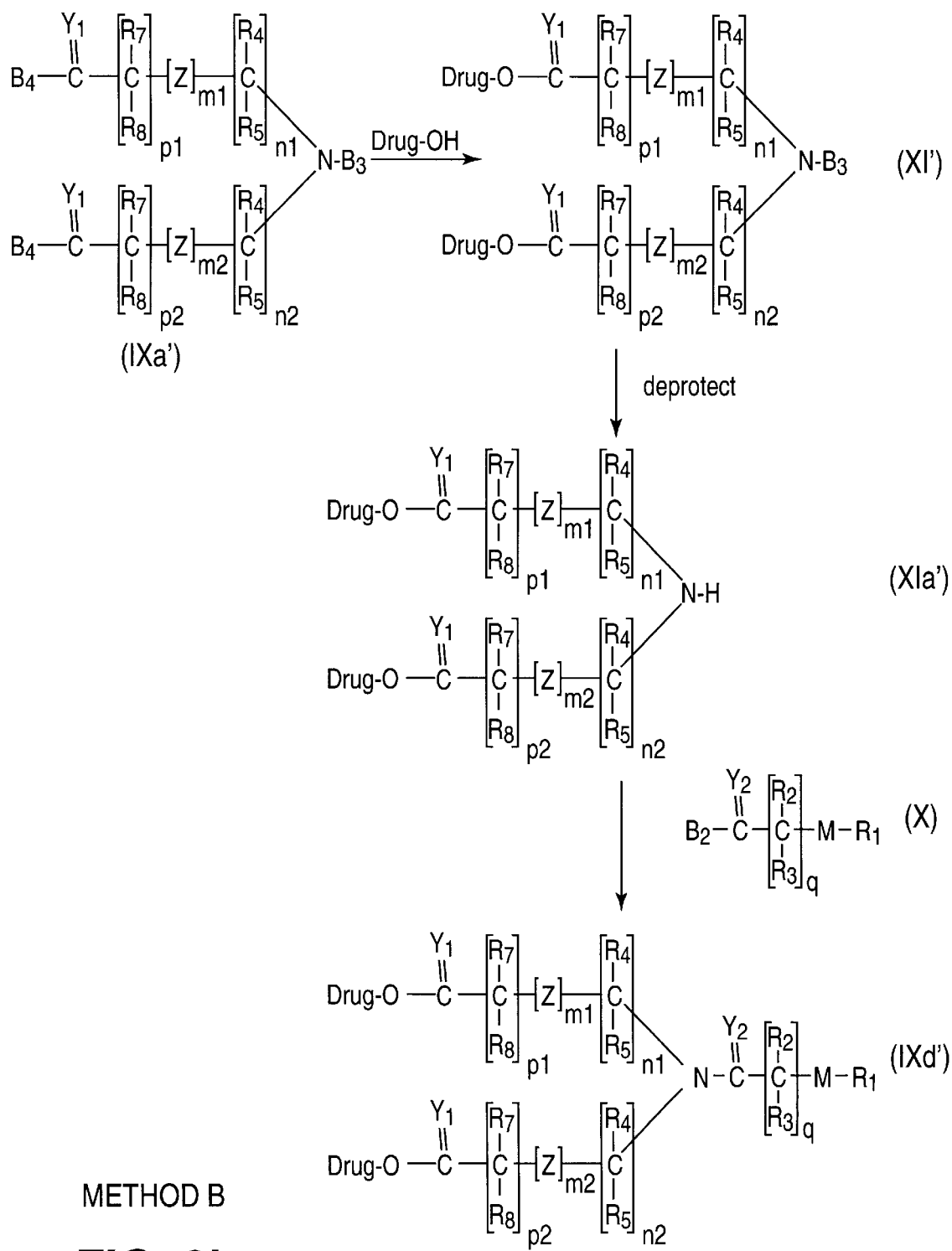
Figure 3:
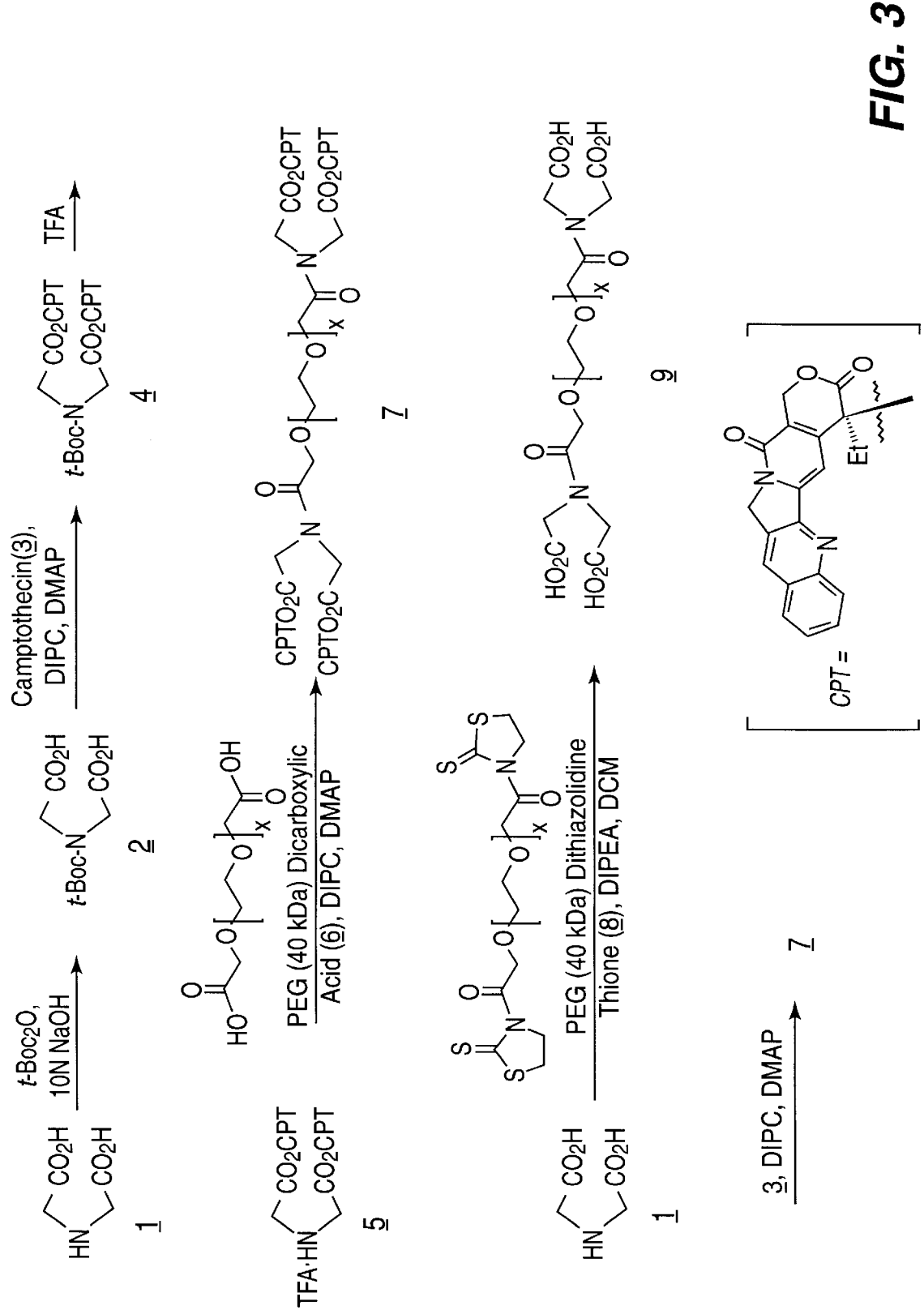
Figure 4:
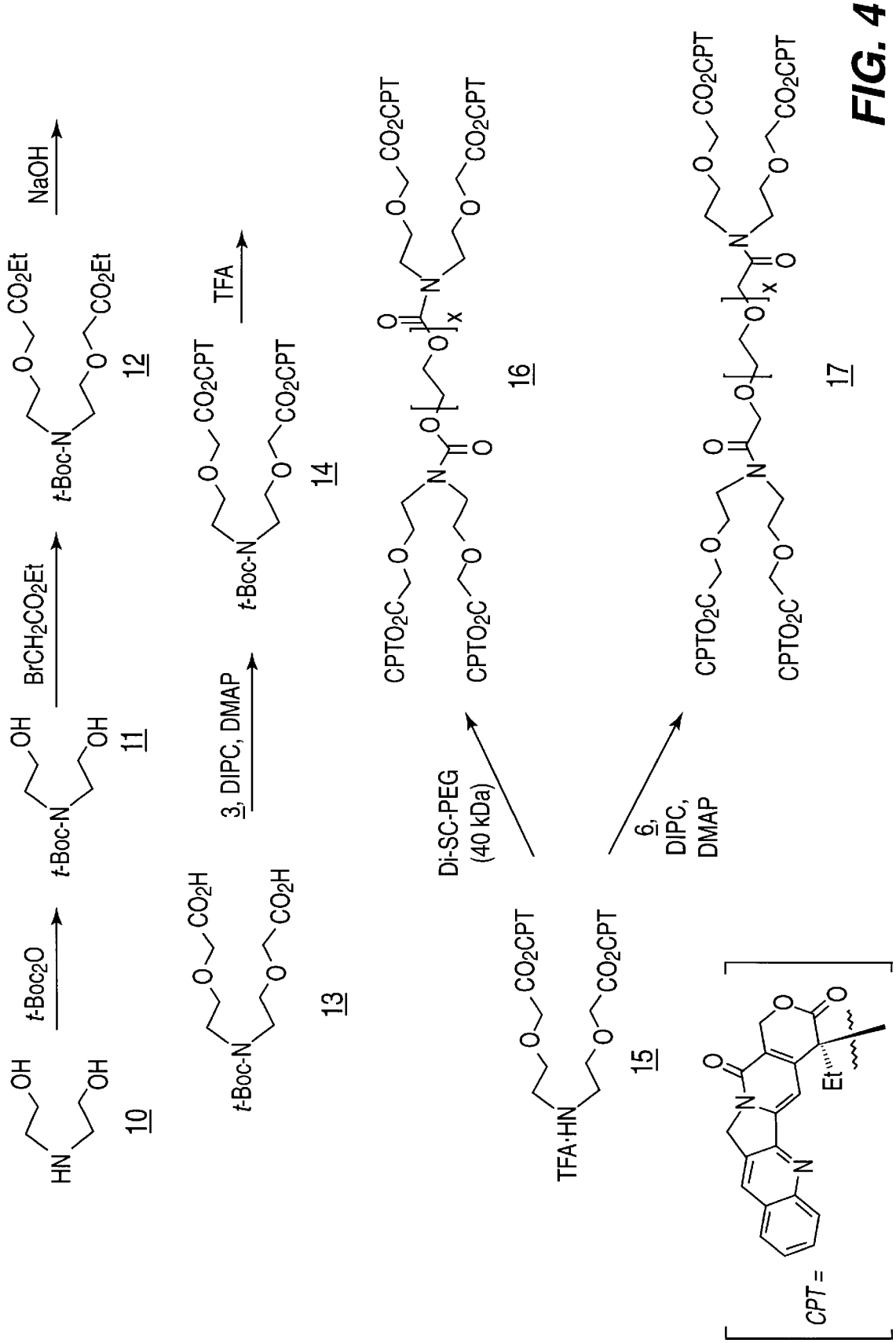
Figure 5:
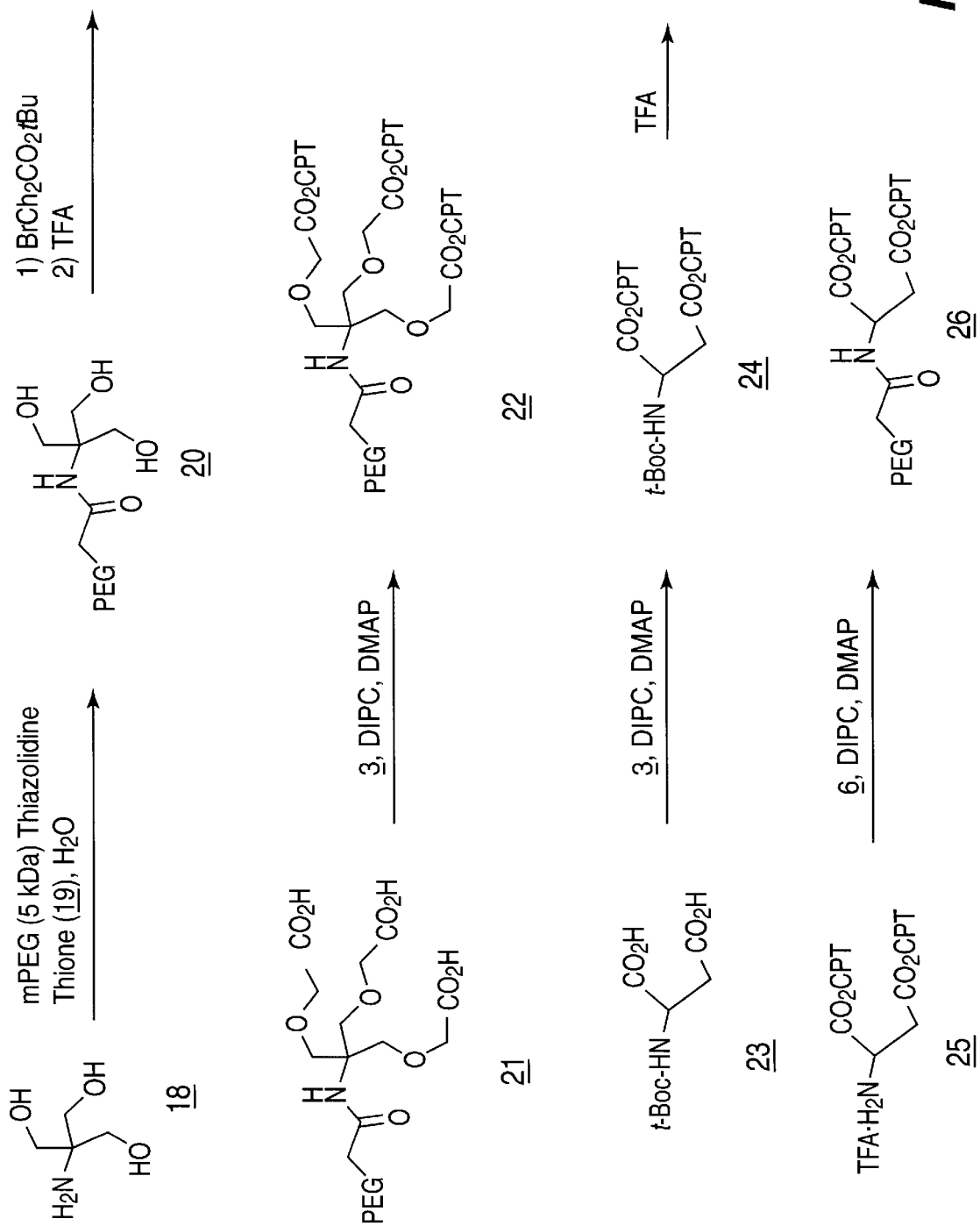
Figure 6:
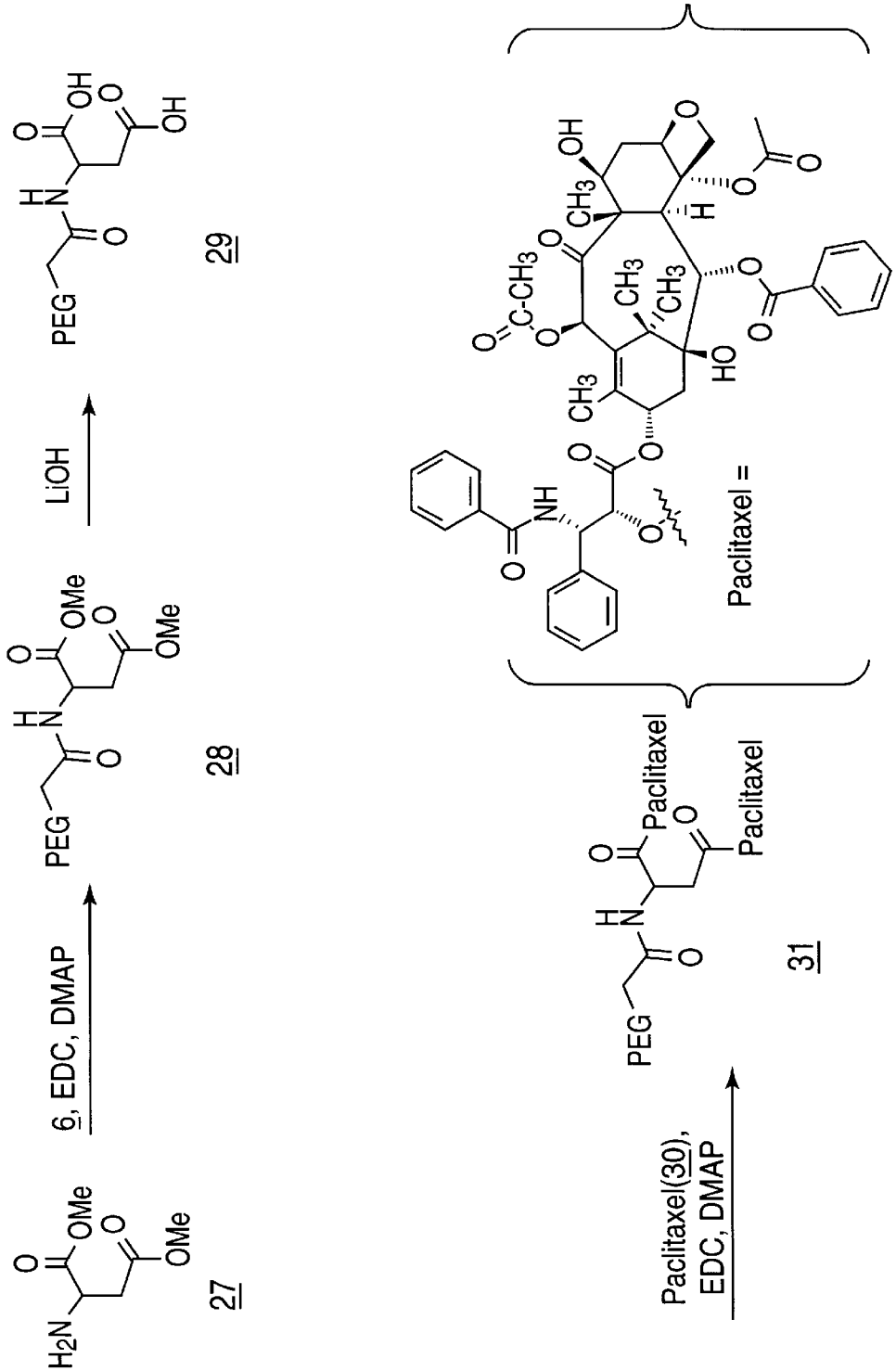
Figure 7:
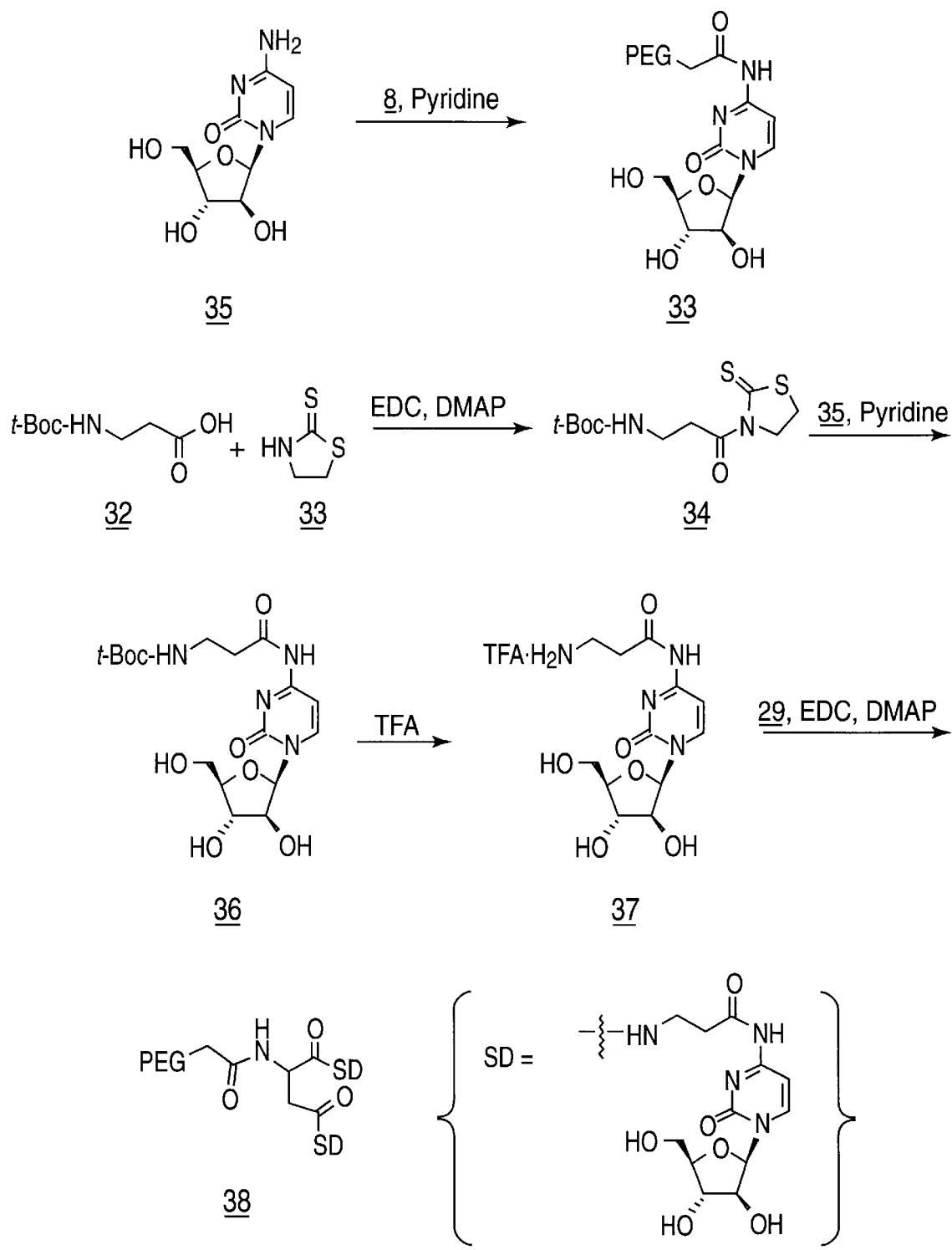

The prodrugs of the present invention can be prepared in at least two general fashions. In the first method, schematically illustrated in FIGS. 1a (symmetrical branches) and 1b (asymmetrical branches), the polymer residue is attached to the branching groups and thereafter the biologically active moiety or drug, e.g. Drug—OH or Drug—$NH_2$ is attached to the polymeric terminal branches. In the second method, the biologically active moiety or drug, e.g. Drug—OH or Drug-$NH_2$ is attached to the branching groups and thereafter, the resultant intermediate is attached to the polymeric residue. FIGS. 1a and 2a schematically illustrate methods in which symmetrical branches are used. Methods in which asymmetrical branches are used are illustrated in FIGS. 1b and 2b.

1. First Method

According to a first method, the branched amine-containing group is provided in a protected form (IX):

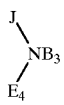

wherein $E_4$ and J are as defined above and $B_3$ is a cleavable or reversible protecting group. An example of a compound of formula (IX) is tBoc aspartic acid. Suitable protecting groups useful for this purpose may be any of a variety of organic moieties known to those of ordinary skill in the art and include, without limitation, t-Boc (tert-butyloxycarbonyl), Cbz (carbobenzyloxy) and TROC (trichloroethoxycarbonyl). In FIG. 1a, compound (IXa) shows J as

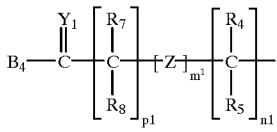

and $E_4$ as

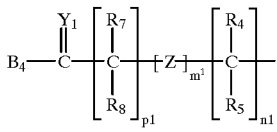

where $B_4$ is OH and all other variables are as defined above.

The protecting group is removed by treatment of (IXa) with a strong acid such as trifluoroacetic acid (TFA) or other haloacetic acid, HCl, sulfuric acid, etc., or by using catalytic hydrogenation. The resulting unprotected amine terminal group (IXb1)

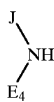

is then reacted with an activated polymer of Formula (X):

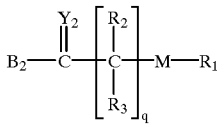

wherein M, (q) and $R_{1-3}$ are as defined above, $Y_2$ is O or S and $B_2$ is a leaving group which is capable of reacting with an unprotected amine, such as an activated carbonate moiety like p-nitrophenyl or succinimidyl carbonate; a thiazolidine thione or other art recognized activating group to form (IXc). In the final synthesis step, a biologically active moiety having an available OH or $NH_2$ group is reacted with (IXc) to form the polymeric transport form (IXd).

Attachment of the B moiety, e.g. Drug—OH or Drug—$NH_2$ is preferably carried out in the presence of a coupling agent. A nonlimiting list of suitable coupling agents include 1,3-diisopropylcarbodiimide (DIPC), any suitable dialkyl carbodiimides, 2-halo-1-alkyl-pyridinium halides, (Mukaiyama reagents), 1-(3-dimethylaminopropyl)-3-ethyl carbodiimide (EDC), propane phosphonic acid cyclic anhydride (PPACA) and phenyl dichlorophosphates, etc. which are available, for example from commercial sources such as Sigma-Aldrich Chemical, or synthesized using known techniques.

FIG. 1b shows a similar reaction scheme except that asymmetric branches are used, i.e. J is the same as in FIG. 1a and $E_4$ is

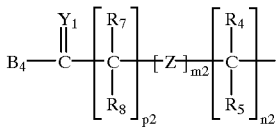

where at least one of (m2), (n2) and (p2) is not the same as (m1), (n1) and (p1), respectively. While not illustrated in FIGS. 1a and 1b, the reaction scheme for attaching biologically active moieties having an available $NH_2$ group such as a protein or enzyme proceeds in a similar manner. All variables shown in the schematics of FIGS. 1a and 1b are the same as that previously defined herein.

Preferably the substituents are reacted in an inert solvent such as methylene chloride, chloroform, toluene, DMF or mixtures thereof. The reaction also preferably is conducted in the presence of a base, such as dimethylaminopyridine, diisopropylethylamine, pyridine, triethylamine, etc. to neutralize any acids generated and at a temperature from 0° C. up to about 22° C. (room temperature).

2. Second Method

Turning now to the second method illustrated in FIGS. 2a and 2b, an alternative synthetic technique is shown using the same moieties for J and $B_4$ as that which was used in the first method. In this embodiment, the protected intermediate (IX) is reacted with a B moiety, e.g. Drug—OH as shown or Drug—$NH_2$, prior to being deprotected. This results in the formation of a linkable ester-containing moiety (XI) which is then subjected to deprotecting to give (XIa) and polymer conjugating steps described above in the first method A to form the polymer transport form (IXd). FIG. 2a shows the formation of symmetrical terminally branched conjugates while FIG. 2b shows the formation of asymmetrical terminally branched conjugates. Amine-containing prodrugs can be made in the same way.

Regardless of the synthesis selected, some of the preferred compounds which result from the synthesis techniques described herein include:

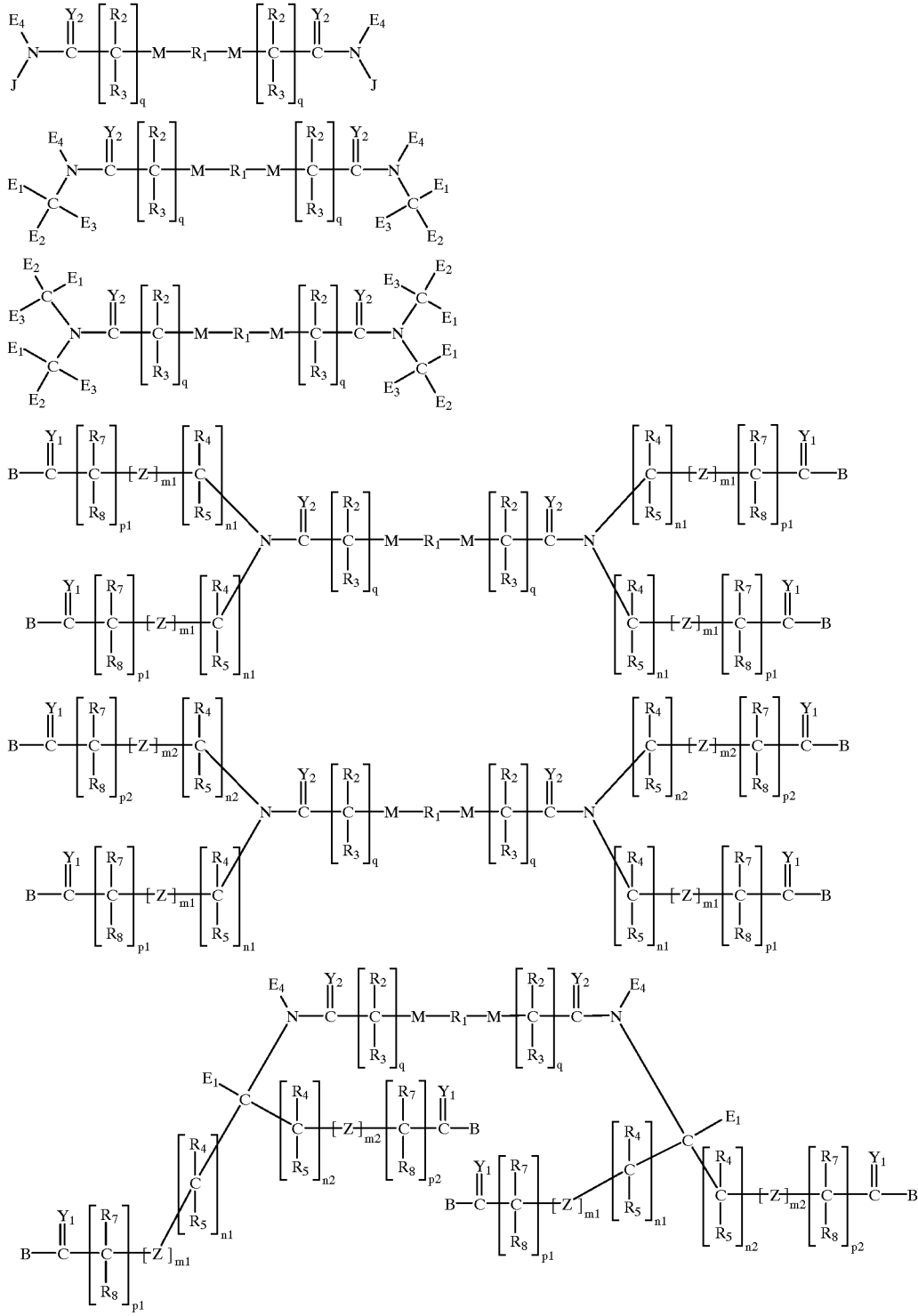

where all variables are as previously defined. In addition, some compounds prepared in accordance with preferred embodiments of the invention include:

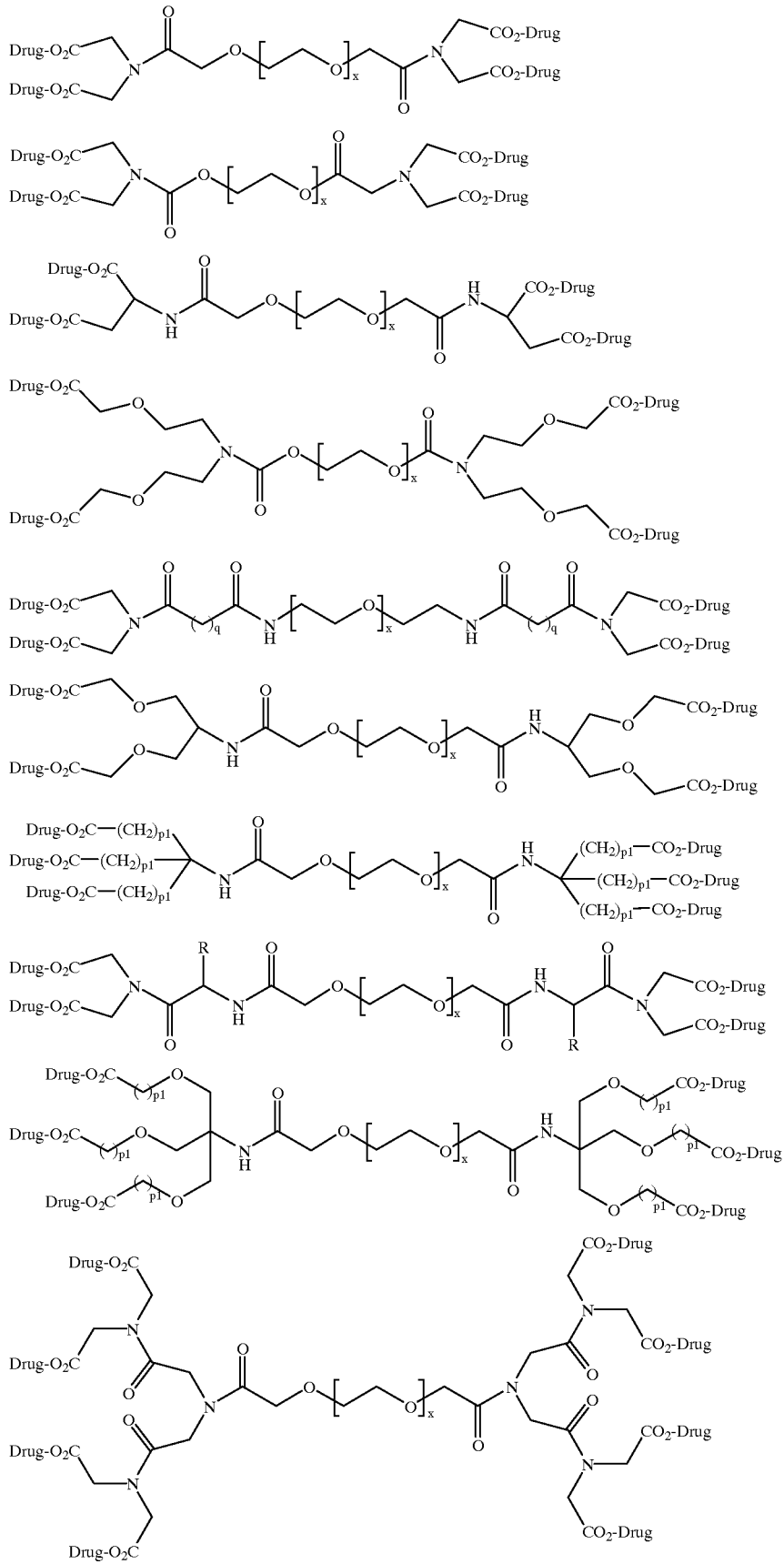

-continued
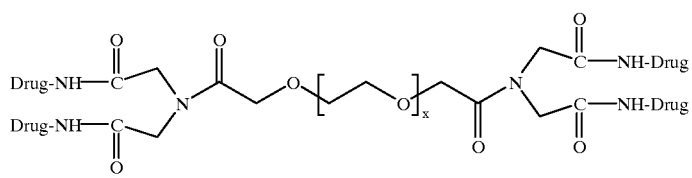
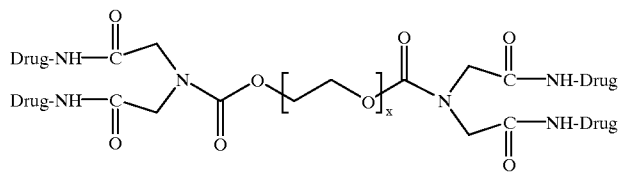
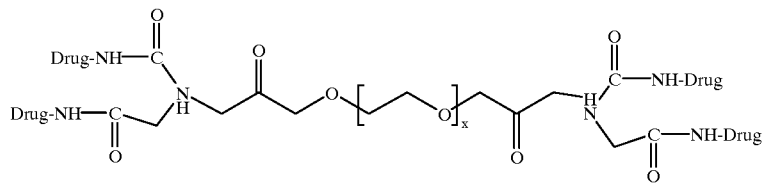
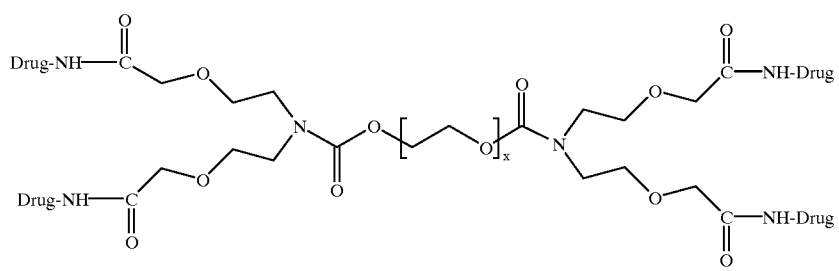
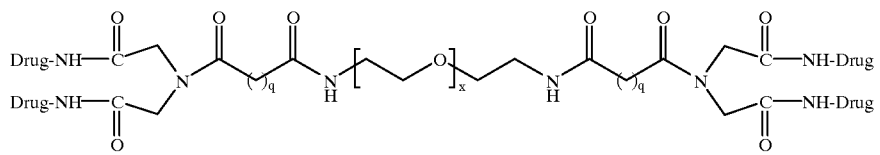
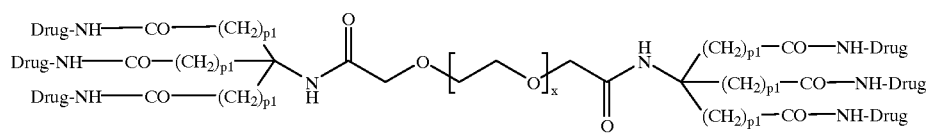
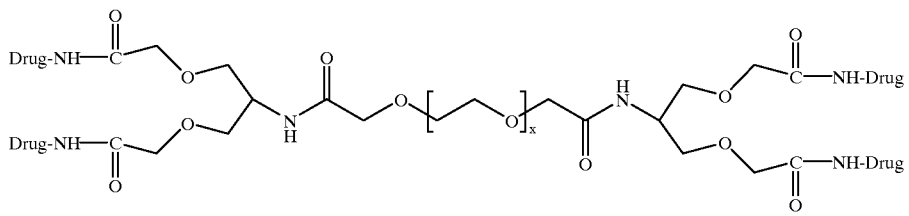
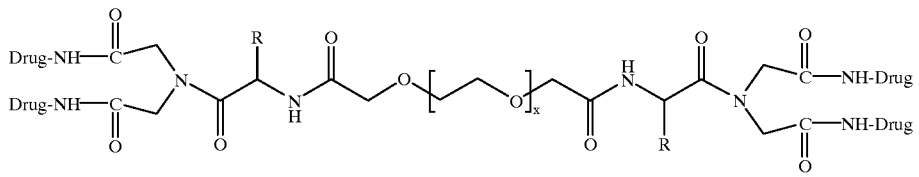

-continued

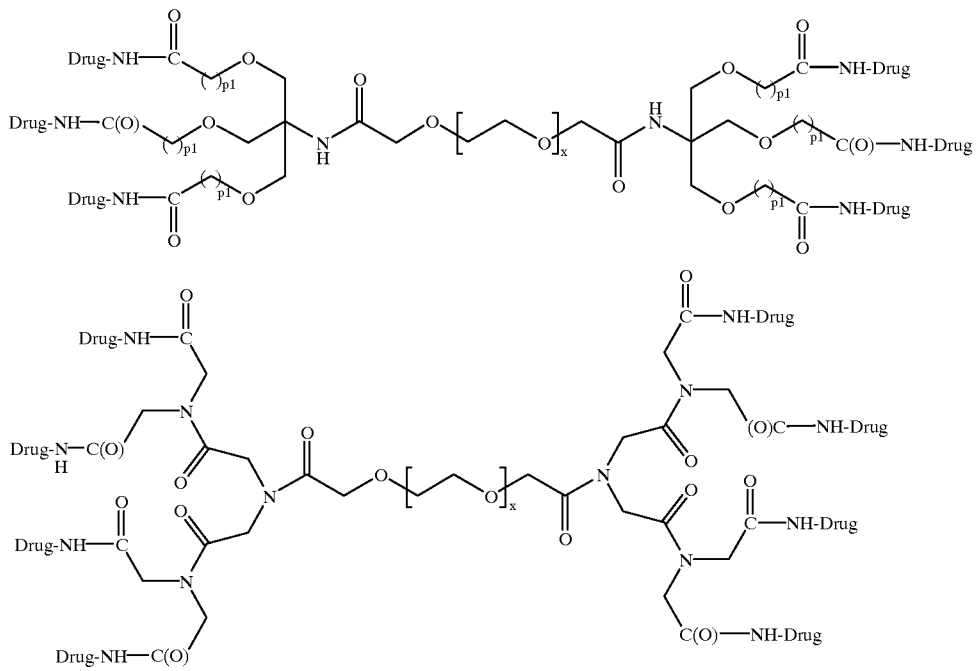

wherein (x) represents the degree of polymerization and "Drug" represents a residue of a hydroxyl- or amine-containing biologically active compound which has undergone a substitution reaction which results in the attachment of the biologically active moiety to the branched polymer.

G. METHODS OF TREATMENT

Another aspect of the present invention provides methods of treatment for various medical conditions in mammals. The methods include administering to the mammal in need of such treatment, an effective amount of a prodrug, such as a camptothecin-20-PEG ester, which has been prepared as described herein. The compositions are useful for, among other things, treating neoplastic disease, reducing tumor burden, preventing metastasis of neoplasms and preventing recurrences of tumor/neoplastic growths in mammals.

The amount of the prodrug administered will depend upon the parent molecule included therein. Generally, the amount of pro drug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, however, prodrug taxanes are administered in amounts ranging from about 5 to about 500 mg/m² per day, based on the amounts of the taxane moiety. Camptothecin prodrugs are also administered in amounts ranging from about 5 to about 500 mg/m² per day. The range set forth above is illustrative and those skilled in the art will determine the optimal dosing of the prodrug selected based on clinical experience and the treatment indication. Actual dosages will be apparent to the artisan without undue experimentation.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administer ed to mammals in need thereof

H. EXAMPLES

The following examples serve to provide further appreciation of the invention but are not meant in any way to restrict the effective scope of the invention. The underlined and bold-faced numbers recited in the Examples correspond to those shown in the Figures.

Example 1

Compound 2: N-t-Boc-iminodiacetic Acid

A mixture of iminodiacetic acid (1, 2 g, 15.03 mmol), di-t-butyl dicarbonate (3.9 g, 18.0 mmol), and sodium hydroxide (0.721 g, 18.0 mmol) in water (50 mL) was stirred at room temperature for 18 hours. The reaction solution was washed with 20 mL of methylene chloride ($CH_2Cl_2$) followed by adjusting pH to 2.5 with 6 N HCl. The resulting mixture was extracted with ethyl acetate (2×300 mL) and the combined organic layer was dried over anhydrous magnesium sulfate ($MgSO_4$). The solvent was removed in vacuo to give 1.0 g (29%) of 2.

$^1$H NMR (270 MHz, DMSO-$d_6$) δ1.36 (s, 9H), 3.88 (s, 2H), 3.92 (s, 2H), 13.69 (bs, 2H). $^{13}$C NMR (67.80 MHz, DMSO-$d_6$) δ27.84, 49.12, 49.64, 79.59, 154.79, 171.20.

Example 2

Compound 4: Coupling of 2 with Camptothecin(3)

A mixture of 2 (200 mg, 0.86 mmol) and camptothecin (3, 777 mg, 2.2 mmol) in anhydrous $CH_2Cl_2$ (50 mL) was cooled in an ice bath for 30 minutes before adding 1,3-diisopropylcarbodiimide (DIPC, 324 mg, 2.4 mmol) and 4-dimethylaminopyridine (DMAP, 272 mg, 2.2 mmol). The reaction mixture was left in the ice bath overnight and was allowed to warm to room temperature slowly. The solution was filtered and washed with water (20 mL) and 1 N HCl (20 mL). The organic layer was dried over anhydrous MgSO$_4$ and concentrated. The residue was purified by silica gel column chromatography (2.5% methanol in CH$_2$Cl$_2$) to give 432 mg (56%) of 4.

$^1$H NMR (270 MHz, CDCl$_3$) δ1.00 (t, 6H, J=8.1 Hz), 1.20 (s, 3H), 1.22 (s, 3H), 1.38 (s, 3H), 1,44 (s, 3H), 2.17 (m, 4H), 4.01–4.36 (m, 4H), 5.26 (d, 2H, J =13.5 Hz), 5.38 (d, 2H, J=10.1 Hz), 5.41 (d, 2H, J=5.4 Hz), 5.24 (d, 2H, J=8.1 Hz), 7.25 (d, 2H, J=13.5 Hz), 7.37 (s, 2H), 7.62 (t, 2H, J=8.1 Hz), 7.79 (q,2H, J=8.1 Hz), 7.90 (m, 2H), 8.19 (m, 2H), 8.35 (d, 2H, J=10.8 Hz). $^{13}$C NMR (67.80 MHz, CDCl$_3$) δ6 7.59, 22.20, 23.37, 25.35, 28.07, 31.57, 31.75, 49.37, 49.56, 49.97, 64.38, 66.94, 74.94, 76.76, 76.79, 78.82, 81.74, 95.83, 96.69, 119.75, 120.12, 127.86, 128.04, 128.15, 128.36, 129.59, 130.40, 130.60, 130.87, 131.10, 145.65, 145.84, 146.31, 146.40, 148.86, 152.14, 152.30, 154.81, 157.34, 166.83, 167.25, 168.78, 169.07.

Example 3

Compound 5: Deprotection of 4

A solution of 4 (300 mg, 0.34 mmol) in anhydrous CH$_2$Cl$_2$ (5 mL) and trifluoroacetic acid (TFA, 2.5 mL) was stirred at room temperature for 3 hours. The reaction mixture was concentrated and the solid was recrystallized from ethyl ether to give 258 mg (78%) of 5 as a TFA salt.

$^1$H NMR (270 MHz, DMSO-d$_6$) δ0.92 (t, 6H, J=8.1 Hz), 2.16 (q, 4H, J=8.1 Hz), 4.19 (d, 2H, J=16.2 Hz), 4.36 (d, 2H, J=16.2 Hz), 5.26 (s, 4H), 5.54 (s, 4H), 7.22 (s, 2H), 7.71 (t, 2H, J=8.1 Hz), 7.84 (t, 2H, J=8.1 Hz), 8.10 (s, 2H), 8.13 (s, 2H), 8.67 (s, 2H). $^{13}$C NMR (67.80 MHz, DMSO-d$_6$) δ7.47, 30.08, 38.58, 38.88, 39.19, 39.50, 39.81, 40.12, 40.42, 46.81, 50.19, 66.32, 77.37, 95.13, 118.79, 127.71, 127.92, 128.54, 128.68, 129.69, 130.45, 131.62, 144.65, 146.03, 147.80, 152.21, 156.41, 166.76.

Example 4

Compound 7: Pegylation of 5

PEG (40 kDa) dicarboxylic acid (6, 2.0 g, 0.05 mmol) was azeotroped for 2 hours in toluene, followed by removal of the solvent in vacuo. Anhydrous CH$_2$Cl$_2$ (20 mL) was added to the residue followed by the addition of 5 (0.16 g, 0.20 mmol), DIPC (25 mg, 0.20 mmol), and DMAP (25 mg, 0.20 mmol). The reaction mixture was stirred at room temperature overnight followed by removal of the solvent in vacuo. The residue was recrystallized from 2-propanol to yield 0.8 g (69%) of 7 as a white solid.

$^{13}$C NMR (67.80 MHz, CDCl$_3$) δ7.25, 31.43, 49.35, 49.64, 66.80, 68.66–71.16 (PEG), 76.06, 95.57, 119.96, 127.71, 127.89, 128.13, 129.38, 130.34, 130.89, 145.11, 146.09, 148.54, 151.93, 156.94, 166.89, 170.58.

Example 5

Compound 9: Coupling of 1 with PEG (40 kDa) Dithiazolidine Thione (8)

PEG (40 kDa) dithiazolidine thione (8, 1 g, 0.025 mmol) is added to the mixture of 1 (14 mg, 0.11 mmol) and N,N-diisopropylethylamine (DIPEA, 37 μL, 0.20 mmol) in anhydrous CH$_2$Cl$_2$ (15 mL). The mixture is stirred at room temperature overnight. The solvent is removed under reduced pressure and the residue is recrystallized from 2-propanol to give 9.

Example 6

Compound 7 from Compound 9

DIPC (13 mg, 0.10 mmol) is added to the mixture of 9 (1.0 g, 0.025 mmol), DMAP (13 mg, 0.10 mmol), and 3,o (35 mg, 0.1 mmol) in anhydrous CH$_2$Cl$_2$ (20 mL). The solution is stirred at room temperature overnight followed by removal of the solvent in vacuo. The residue is recrystallized from 2-propanol (80 mL) to give 7.

Example 7

Compound 11: N-t-Boc-diethanolamine

A solution of di-t-butyl dicarbonate (26.46 g, 0.12 mol) in chloroform (50 mL) was added to the solution of diethanolamine (10, 12.63 g, 0.12 mol) in chloroform (50 mL) slowly at room temperature. The reaction solution was stirred at room temperature for 1 hour, followed by washing with water (30 mL) and the organic layer was dried over anhydrous MgSO$_4$. The solvent was removed under reduced pressure to give 11 (20 g, 83%).

$^1$H NMR (270 MHz, CDCl$_3$) δ1.46 (s, 9H), 3.41 (bs, 4H), 3.76 (bs, 4H), 4.69 (bs, 2H). $^{13}$C NMR (67.80 MHz, CDCl$_3$) δ28.30, 52.22, 61.63, 80.13, 156.22.

Example 8

Compound 12

Compound 11 (9.5 g, 46.34 mmol) was dissolved in anhydrous toluene (200 mL) by warming and the solution cooled to −20° C. followed by the addition of potassium t-butoxide (1M solution in t-butanol, 70 mL, 70 mmol). The mixture was stirred at −20° C. for 5 hours and then cooled to −30° C. Ethyl bromoacetate (30.96 g, 185.35 mmol) was added to the solution and the reaction mixture was stirred at −15° C. for 3 hours. The solution was washed with water (50 mL) and the organic layer was dried over anhydrous MgSO$_4$. The solvent was removed in vacuo to give a crude product which was purified by silica gel column chromatography (ethyl acetate/hexane=1:1, v/v) to give 8.2 g (48%) of 12.

$^1$H NMR (270 MHz, CDCl$_3$) δ1.28 (t, 6H, J=5.4 Hz), 1.45 (s, 9H), 3.51 (bs, 4H), 3.67 (bs, 4H), 4.08 (s, 4H), 4.21 (q, 4H, J=5.4 Hz). $^{13}$C NMR (67.80 MHz, CDCl$_3$) δ13.95, 28.15, 47.61, 60,49, 68.16, 69.06, 79.42, 155.14, 170.02.

Example 9

Compound 13

A solution of NaOH (10 g, 250 mmol) in water (10 mL) and ethanol (100 mL) was added to a solution of 12,0 (8.0 g, 21.22 mmol) in ethanol (80 mL). The reaction solution was stirred at room temperature for 1.5 hours and cooled to 0° C. The pH was adjusted to 2.5 with 6N HCl. The mixture was filtered and the filtrate was concentrated in vacuo. Chloroform (300 mL) was added to the residue and washed with water (3×50 mL). The organic layer was dried over anhydrous MgSO$_4$ and concentrated under reduced pressure to give 5.0 g (73%) of 13.

$^1$H NMR (270 MHz, CDCl$_3$) δ1.45 (s, 9H), 3.51 (bs, 4H), 3.71 (bs, 4H), 4.13 (s, 4H), 9.35 (bs, 2H). $^{13}$C NMR (67.80 MHz, CDCl$_3$) δ28.35, 48.13, 67.97, 70.24, 80.54, 155.93, 173.95.

Example 10

Compound 14: Coupling of 13 with 3

A mixture of 13 (2 g, 6.23 mmol), 3 (5.643 g, 16.20 mmol), DMAP (1.979 b 15 g, 16.20 mmol), and DIPC (2.041 g, 16.20 mol) in anhydrous CH$_2$Cl$_2$ (50 mL) was stirred at room temperature for 20 hours. The reaction mixture was filtered and the filtrate washed with water (30 mL) and dried over anhydrous MgSO$_4$. The solution was concentrated to give crude product which was purified by silica gel column chromatography (2.5% methanol in $CH_2Cl_2$) to give 14 as a light yellow solid (2.45 g, 40%).

$^1$H NMR (270 MHz, $CDCl_3$) δ0.96 (t, 6H, J=8.1 Hz), 1.38 (s, 9H), 2.20 (qd, 4H, J=13.5, 8.1 Hz), 3.47 (bs, 4H), 3.63 (bs, 4H), 4.25 (s, 4H), 5.24 (s, 4H), 5.39 (d, 2H, J=13.5 Hz), 5.66 (d, 2H, J=13.5 Hz), 7.19 (s, 2H), 7.65 (t, 2H, J=6.8 Hz), 7.80 (t, 2H, J=6.8 Hz), 7.93 (d, 2H, J=8.1 Hz), 8.2 (d, 2H, J=8.1 Hz), 8.36 (s, 2H). $^{13}$C NMR (67.80 MHz, $CDCl_3$) δ7.46, 28.27, 31.70, 47.53, 47.74, 49.83, 67.06, 67.84, 70.37, 76.22, 79.68, 95.76, 120.19, 127.92, 128.07, 128.36, 129.53, 130.55, 131.07, 145.29, 146.30, 148.71, 152.15, 155.25, 157.18, 167.09, 169.36.

Example 11
Compound 15: Deprotection of 14

Compound 14 (0.74 g, 0.75 mmol) was dissolved in $CH_2Cl_2$ (10 mL) and TFA (5 mL). The reaction solution was stirred at room temperature for 2 hours and concentrated under reduced pressure. The residue was recrystallized from $CH_2Cl_2$-ethyl ether to give 0.6 g (100%) of 15 as a TFA salt.

$^1$H NMR (270 MHz, $CDCl_3$) δ0.9, 2.1, 3.3, 3.9, 4.4, 5.2, 5.4, 5.6, 7.2, 7.6, 7.8, 7.9, 8.1, 8.4. $^{13}$C NMR (67.80 MHz, $CDCl_3$) δ7.17, 31.20, 46.85, 49.77, 53.40, 66.43, 67.61, 76.79, 95.46, 119.51, 127.70, 127.94, 128.43, 129.04, 130.36, 131.05, 145.00, 146.23, 148.29, 151.86, 156.87, 166.85, 169.49.

Example 12
Compound 16: Coupling of 15 with Di-SC-PEG (40 kDa)

A mixture of 15 (79,8 mg, 0,09 mmol), di-SC-PEG (40 kDa, 1.0 g, 0.025 mmol), and DMAP (11.1 mg, 0.09 mmol) in anhydrous chloroform (20 mL) was stirred at room temperature overnight. The solvent was removed in vacuo and the residue was recrystallized from 2-propanol (80 mL) to give 0.92 g (92%) of 16.

$^{13}$C NMR (67.80 MHz, $CDCl_3$) δ7.15, 31.54, 47.68, 49.63, 64.17, 66.73, 67.92, 69.13–71.28 (PEG), 76.16, 95.33, 120.01, 127.57, 127.83, 127.97, 128.39, 129.45, 130.15, 130.71, 145.28, 146.22, 148.70, 152.12, 155.74, 156.94, 166.52, 168.90.

Example 13
Compound 17: Coupling of 15 with PEG (40 kDa) Dicarboxylic Acid (6)

Compound 6 (3 g, 0.075 mmol) was azeotroped for 2 hours in 90 mL of toluene. The solvent was removed in vacuo and the residue was dissolved in 50 mL of anhydrous $CH_2Cl_2$. Compound 15 (263.5 mg, 0.3 mmol), DMAP (45.7 mg, 0.38 mmol), and DIPC (37.7 mg, 0.30 mol) were added to the solution and the reaction mixture was stirred at room temperature overnight. The reaction solution was diluted with 100 mL of $CH_2Cl_2$ and washed with 1N HCl (2×20 mL) and water (20 mL). The organic layer was dried over anhydrous $MgSO_4$ and the solvent was removed under reduced pressure. The residue was recrystallized from 2-propanol (100 mL) to give 2.44 g (80%) of 17.

$^1$H NMR (270 MHz, $CDCl_3$) δ1.01, 2.2, 2.9, 3.2–3.9 (PEG), 4.2, 5.2, 5.3, 5.7, 7.15, 7.65, 7.8, 7.95, 8.2, 8.5. $^{13}$C NMR (67.80 MHz, $CDCl_3$) δ66.91, 31.01, 45.05, 47.50, 49.33, 66.36, 67.21, 67.30–71.16 (PEG), 75.62, 75.72, 77.92, 94.86, 119.31, 119.38, 127.31, 127.53, 127.63, 127.99, 128.85, 129.93, 130.74, 144.61, 145.83, 148.05, 151.54, 156.45, 166.34, 168.47, 168.55, 169.23.

Example 14
Compound 20: Coupling of TRIS (18) with mPEG (20 kDa) Thiazolidine Thione (19).

mPEG (20 kDa) thiazolidine thione (19, 4 g, 0.2 mmol) was added to a solution of tris(hydroxymethyl)aminomethane (TRIS, 18, 2.4 g, 20 mmol) in water (60 mL). The mixture was stirred at room temperature overnight, followed by extraction with $CH_2Cl_2$ (2×50 mL). The combined organic layer was washed with brine (60 mL) and dried over anhydrous $MgSO_4$. The solvent was removed under reduced pressure and the residue was recrystallized from 2-propanol to give 2.0 g (50%) of 20.

$^{13}$C NMR (67.80 MHz, $CDCl_3$) δ58.33, 60.99, 62.31, 69.91–71.28 (PEG), 170.51.

Example 15
Compound 21

A solution of 20 (10 g, 2 mmol) in 100 mL of toluene is azeotroped for 2 hours and is cooled to 35° C. followed by the addition of 10.5 mL (10.5 mmol) of 1.0 M potassium t-butoxide in t-butanol. The mixture is stirred for 1 hour at 35° C. followed by the addition of 3.9 g (20 mmol) of t-butyl bromoacetate. The reaction mixture is stirred at 40° C. overnight, filtered through celite and solvent removed in vacuo. The residue is recrystallized from chilled $CH_2Cl_2$-ethyl ether to yield ester of 20. The ester is dissolved in $CH_2Cl_2$ (100 mL) and TFA (50 mL). The reaction solution is stirred at room temperature for 2 hours and concentrated under reduced pressure. The residue is recrystallized from $CH_2Cl_2$-ethyl ether to give 21.

Example 16
Compound 22: Coupling of 3 with 21

Compound 21 (3 g, 0.56 mmol) is azeotroped for 2 hours in 90 mL of toluene. The solvent is removed in vacuo and the residue is dissolved in 60 mL of anhydrous $CH_2Cl_2$. Compound 3 (1.17 g, 3.4 mmol), DMAP (829.6 mg, 6.8 mmol), and DIPC (1.37 g, 13.6 mmol) are added to the solution and the reaction mixture is stirred at room temperature overnight. The reaction solution is diluted with 100 mL of $CH_2Cl_2$ and washed with 1N HCl (2×20 mL) and water (20 mL). The organic layer is dried over anhydrous $MgSO_4$ and the solvent is removed under reduced pressure. The residue is recrystallized from 2-propanol (300 mL) to give 22.

Example 17
Compound 24: Coupling of 3 with N-t-Boc-L-Aspartic Acid (23)

DIPC (0.72 g, 5.8 mmol) was added to a solution of N-t-Boc-L-aspartic acid (23, 1.34 g, 5.8 mmol), 3 (2.0 g, 5.8 mmol), DMAP (0.7 g, 5.8 mmol), and in anhydrous $CH_2Cl_2$ (25 mL) at 0° C. The mixture was allowed to warm to room temperature overnight, followed by washing with 1% aqueous sodium bicarbonate (4×15 mL) and 0.1 N HCl (2×15 mL). The organic layer was dried over anhydrous $MgSO_4$. The solution was concentrated to give a crude product as a solid which was recrystallized in methanol to give 24 (2.1 g, 40%).

$^{13}$C NMR (67.80 MHz, $CDCl_3$) δ7.25, 7.47, 27.20, 27.83, 28.12, 31.30, 31.48, 35.66, 49.74, 66.46, 66.83, 80.11, 96.25, 96.57, 119.64, 119.86, 127.79, 127.91, 128.17, 128.36, 129.48, 129.59, 130.40, 130.92, 145.20, 145.84, 146.05, 148.59, 151.89, 152.07, 155.18, 156.84, 156.92, 166.51, 167.22, 169.68, 169.90.

Example 18
Compound 25: Deprotection of 24

A solution of 24 (500 mg, 0.56 mmol) in anhydrous $CH_2Cl_2$ (5 mL) and trifluoroacetic acid (TFA, 2.5 mL) was stirred at room temperature for 1 hour, followed by addition of ethyl ether (40 mL). The solid was filtered and washed with ethyl ether to give 25 (0.4 g, 75%).

Example 19
Compound 26: Coupling of 25 with 6

PEG (40 kDa) dicarboxylic acid (6, 1.0 g, 0.025 mmol) was azeotroped for 2 h in toluene, followed by removal of the solvent in vacuo. Anhydrous $CH_2Cl_2$ (20 mL) was added to the residue followed by the addition of 25 (94 mg, 0.10 mmol), DIPC (13 mg, 0.10 mmol), and DMAP (25 mg, 0.20 mmol). The reaction mixture was stirred at room temperature overnight followed by removal of the solvent in vacuo. The residue was recrystallized from 2-propanol to yield 0.81 g (81%) of 26 as a white solid.

Example 20
Compound 28

A mixture of 6 (5 g, 0.125 mmol), L-aspartic acid dimethylester HCl (27, 98.5 mg, 0.50 mmol), 1-ethyl-3-(3-dimethylaminopropyl)carbodiimide hydrochloride (EDC, 191 mg, 1.0 mmol), and DMAP (122 mg, 1.0 mmol) in anhydrous $CH_2Cl_2$ (80 mL) was stirred at room temperature overnight. The solvent was removed and the residue was recrystallized from 2-propanol to give 4.2 g (84%) of 28.

$^{13}$C NMR (67.80 MHz, $CDCl_3$) δ35.08, 47.08, 51.00, 51.72, 62.00–71.25 (PEG), 168.87, 169.85, 170.01.

Example 21
Compound 29

Compound 28 (3.8 g, 0.094 mmol) and lithium hydroxide (24 mg, 0.57 mmol) were stirred in water (20 mL) for 6 hours, followed by acidification with 1N HCl to adjust the pH to 3. The product was extracted to $CH_2Cl_2$ and recrystallized with chilled $CH_2Cl_2$-ether to give 3.5 g (92%) of 29.

$^{13}$C NMR (67.80 MHz, $CDCl_3$) δ34.96, 46.80, 67.64–70.72 (PEG), 168.74, 170.35, 170.61.

Example 22
Compound 31

A mixture of 29 (1.0 g, 0.025 mmol), paclitaxel (30, 170 mg, 0.20 mmol), EDC (76 mg, 0.4 mmol), and DMAP (76 mg, 0.6 mmol) in anhydrous $CH_2Cl_2$ (20 mL) was stirred at room temperature for 16 hours. The mixture was concentrated in vacuo and the residue was recrystallized from 2-propanol to give 0.95 g (95%) of 31.

$^{13}$C NMR (67.80 MHz, $CDCl_3$) δ8.92, 13.75, 13.95, 20.08, 21.34, 21.84, 22.12, 34.75, 35.43, 42.47, 45.33, 47.09, 51.49, 51.64, 57.59, 69.80–71.10 (PEG), 74.26, 74.70, 75.56, 75.80, 77.84, 77.97, 80.31, 83.58, 125.65, 125.82, 126.25, 126.74, 126.84, 127.78, 128.00, 128.18, 128.54, 128.75, 129.45, 131.15, 132.38, 132.54, 132.72, 132.84, 135.59, 136.27, 141.11, 165.79, 165.86, 166.49, 167.59, 167.69, 169.16, 169.26, 169.41, 169.93, 202.70.

Example 23
Compound 34

A mixture of t-Boc-β-Alanine (32, 200 mg, 1.06 mmol), 2-mercapto-thiazolidine (33, 252 mg, 2.12 mmol), EDC (407 mg, 2.12 mmol), and DMAP (516 mg, 4.23 mmol) in anhydrous $CH_2Cl_2$ (10 mL) is stirred at room temperature overnight. The reaction mixture is diluted with 40 mL of $CH_2Cl_2$ and washed twice with 1% $NaHCO_3$ (25 mL) and twice with 1N HCl. The organic layer is dried over anhydrous sodium sulfate and the solvent is removed in vacuo to give 34.

Example 24
Compound 36

A mixture of 34 (1.79 g, 6.17 mmol) and 35 (4.5 g, 18.5 mmol) in anhydrous pyridine (125 mL) is stirred at 40° C. overnight. The reaction mixture is concentrated in vacuo and the residue is purified by column chromatography to give 36.

Example 25
Compound 37

Compound 36 (1 g) is dissolved in TFA (10 mL) and $CH_2Cl_2$ (10 mL) and the solution stirred at room temperature for 2 hours. The solvent is removed in vacuo and the product precipitated by adding anhydrous ethyl ether to give 37 as the TFA salt.

Example 26
Compound 38

A mixture of 29 (1.0 g, 0.025 mmol), 37 (106 mg, 0.20 mmol), EDC (76 mg, 0.4 mmol), and DMAP (76 mg, 0.6 mmol) in anhydrous $CH_2Cl_2$ (20 mL) is stirred at room temperature for 16 hours. The mixture is concentrated in vacuo and the residue recrystallized from 2-propanol to give 38.

Example 27
Compound 39

In this example, a polymeric conjugate of gemcitabine is prepared by repeating the procedures of Examples 24–26 using gemcitabine in place of Ara-C (35).

Example 28
Compound 41

PEG 40 kDa diamine hydrochloride (5 g, 0.125 mmol) is dissolved in anhydrous dichloromethane (50 mL) and EDC (95 mg, 0.49 mmol) and DMAP (95 mg, 0.78 mmol) are added. The solution is stirred for 3 hours at room temperature. The dianhydride of diethylenetriaminepentaacetic acid (DADTPA, 134 mg, 0.38 mmol) is added to this solution and the mixture stirred overnight at room temperature. The solvent is removed in vacuo and the residue recrystallized from dichloromethane/ethyl ether to give 40.

A mixture of 40 (1.0 g, 0.025 mmol), 30 (170 mg, 0.20 mmol), and DMAP (76 mg, 0.6 mmol) in anhydrous $CH_2Cl_2$ (20 mL) is stirred at room temperature for 16 hours. The mixture is concentrated in vacuo and the residue is recrystallized from 2-propanol to give 41.

The various publications, patents, patent applications and published applications mentioned in this application are hereby incorporated by reference herein.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

We claim:

1. A compound comprising the formula:

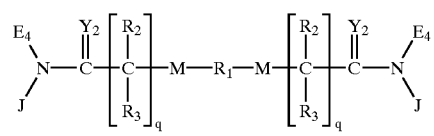

wherein:

J is 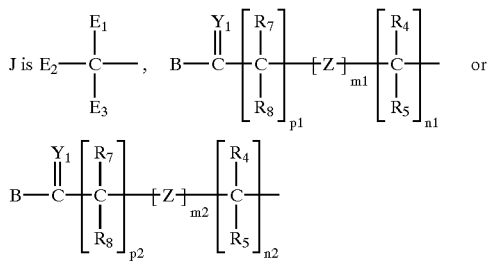

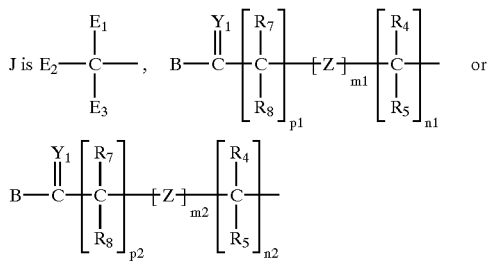

$E_{1-4}$ are independently selected from the group consisting of hydrogen, $C_{1-6}$ alkyls, $C_{3-12}$ branched alkyls. $C_{3-8}$ cycloalkyls, $C_{1-6}$ substituted alkyls, $C_{3-8}$ substituted cycloalkyls, aryls, substituted aryls, aralkyls, $C_{1-6}$, heteroalkyls, substituted $C_{1-6}$ heteroalkyls, $C_{1-6}$ alkoxy, phenoxy, $C_{1-6}$ heteroalkoxy, and at least one of $E_{1-4}$ is

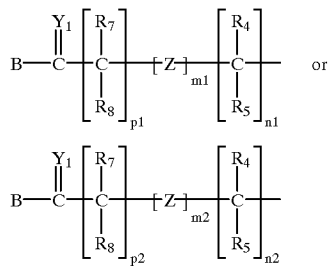

wherein B is a leaving group, OH, a residue of a hydroxyl-containing moiety, a residue of an amine-containing moiety or

wherein $J_1$ is the same as J, or another member of the group defining J and $E_5$ is the same as $E_{1-4}$, or another member of the group defining $E_{1-4}$;

$Y_{1-2}$ are independently O, S or $NR_9$;

M is a heteroatom selected from either X or Q; wherein X is an electron withdrawing group and Q is a moiety containing a free electron pair positioned three to six atoms from $C(=Y_2)$;

$R_{2-5}$ and $R_{7-9}$ are independently selected from the group consisting of hydrogen, $Cl_{1-6}$ alkyls, $C_{3-12}$ branched alkyls, $C_{3-8}$ cycloalkyls, $C_{1-6}$- substituted alkyls, $C_{3-8}$ substituted cycloalkyls, aryls, substituted aryls, aralkyl., $C_{1-6}$ heteroalkyls, substituted $C_{1-6}$ heteroalkyls, $C_{1-6}$ alkoxy, phenoxy and $C_{1-6}$ heteroalkoxy;

(m1) and (m2) are independently zero or one;

(n1), (n2), (p1), (p2) and (q) are independently zero or a positive integer;

Z is an electron withdrawing group; and $R_1$ is a polymeric residue of a substantially non-antigenic polymer having a molecular weight of at least about 20,000 Daltons.

2. The compound of claim 1, wherein $Y_1$ and $Y_2$ are oxygen.

3. The compound of claim 1, wherein $R_{2-5}$, $R_7$ and $R_8$ are hydrogen.

4. The compound of claim 1, wherein X is selected from the group consisting of O, S, SO, $SO_2$, $C(Y_3)$ and $NR_6$, wherein $Y_3$ is selected from the group consisting of O, S and $R_9$, and $R_6$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls.

5. The compound of claim 1, wherein Q is selected from the group consisting of $C_{2-4}$ alkyls, cycloalkyls, aryls, aralkyl groups substituted with a member of the group consisting of NH, O, S, —$CH_2$—C(O)—NH—, and ortho-substituted phenyls.

6. The compound of claim 1, wherein (p1) and (p2) are 1.

7. The compound of claim 1, wherein (n1) and (n2) are individually 1 or 2.

8. The compound of claim 7, wherein (n1) is 1 and (n2) is 2.

9. The compound of claim 1, wherein (m1) and (m2) are 1.

10. The compound of claim 1, wherein (q) is 1.

11. The compound of claim 1, wherein $R_1$ comprises a polyalkylene oxide residue.

12. The compound of claim 11, wherein said polyalkylene oxide residue comprises polyethylene glycol.

13. The compound of claim 1, wherein said polymeric residue has a molecular weight of from about 20,000 to about 40,000.

14. The compound of claim 1, wherein B is a residue of a member of the group consisting of Ara-C, camptothecin, camptothecin analogs, paclitaxel, taxoteres, gemcitabine, podophyllotoxin, fluconazole, ciclopirox, amphotericin B, nystatin, doxorubicin, daunorubicin, maytansinie, vancomycin and erythromycin.

15. A compound of claim 1, having a formula selected from the group consisting of:

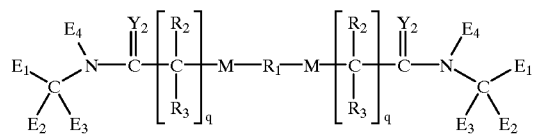

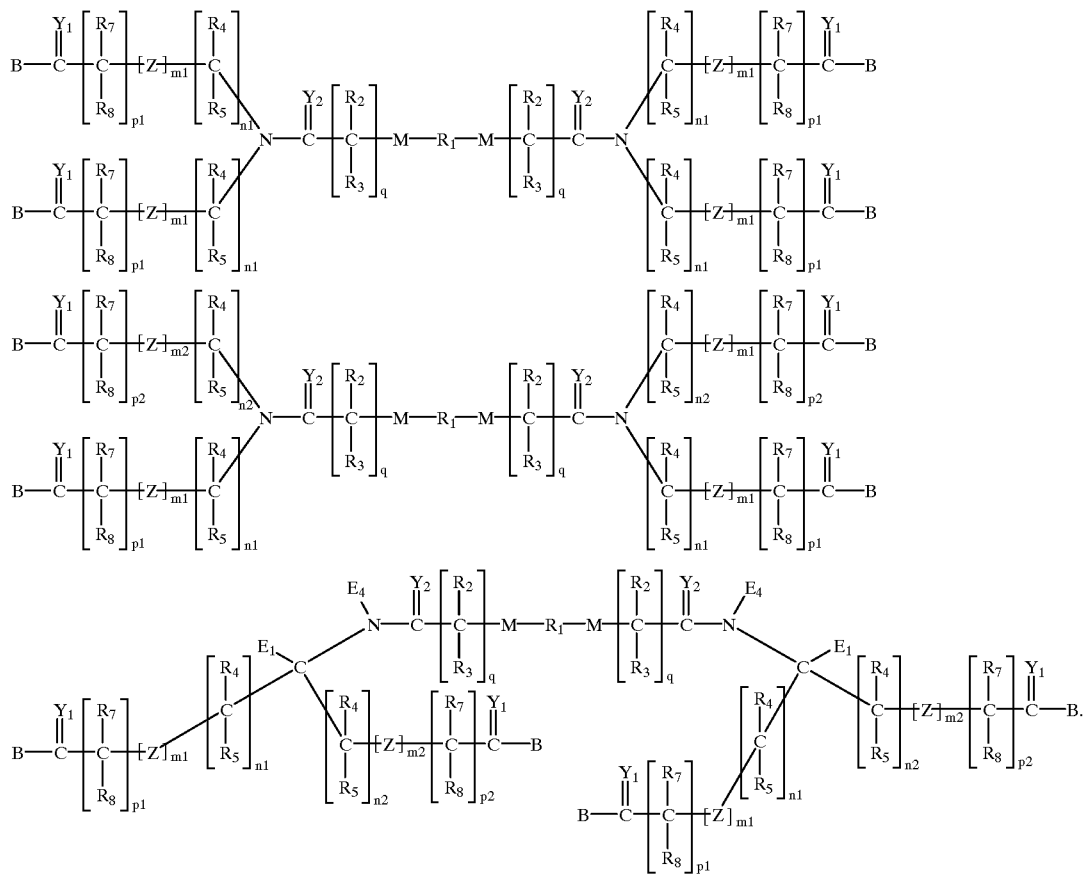
16. A compound of claim 1, having a formula selected from the group consisting of:
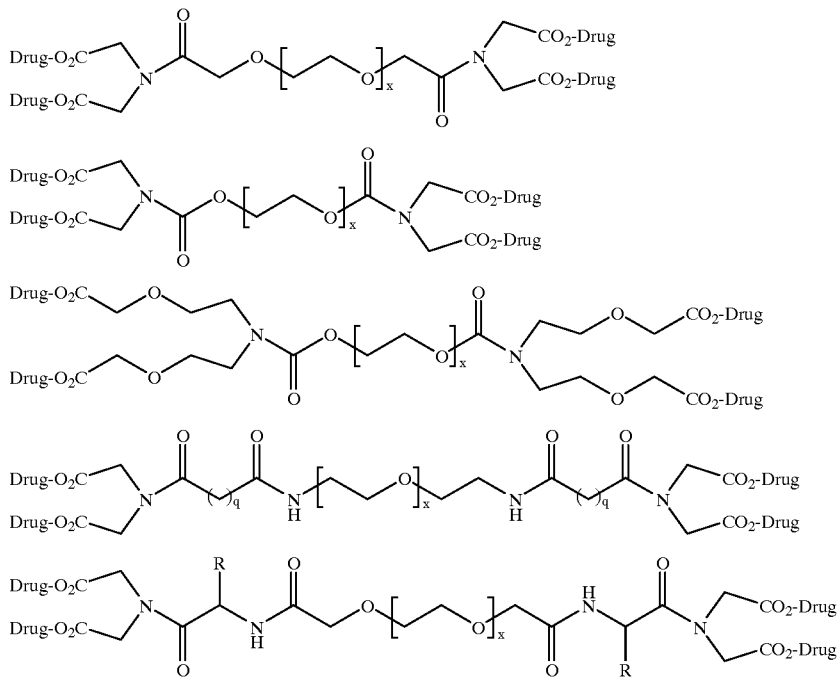

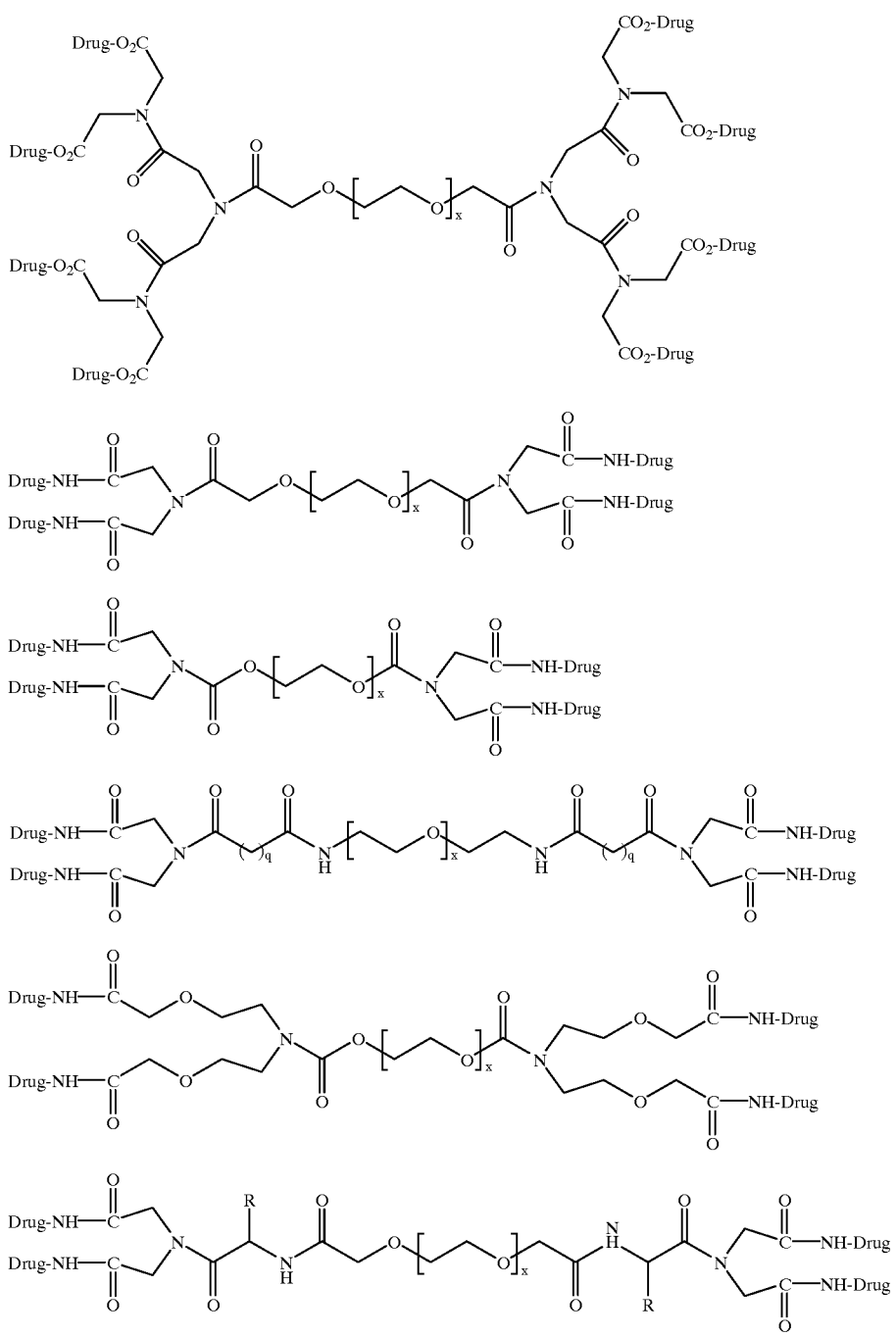

-continued

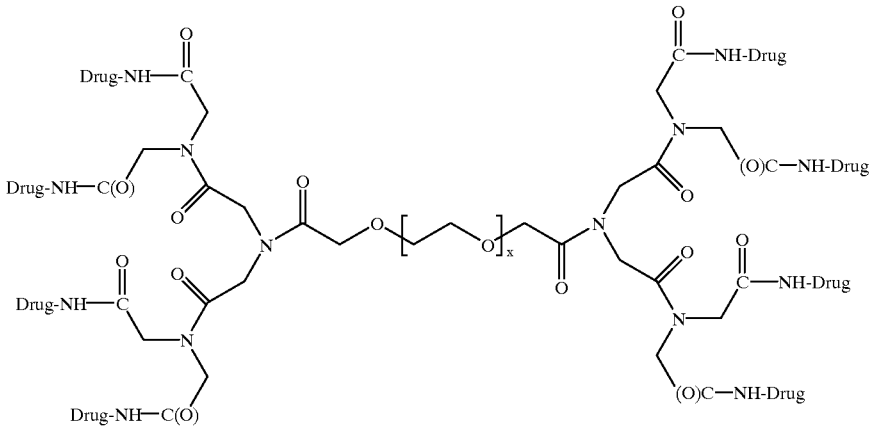

wherein (x) represents the degree of polymerization and "Drug" represents a residue of a hydroxyl- or amine-containing biologically active compound which has undergone a substitution reaction which results in the attachment of the biologically active moiety to the branched polymer.

17. A method or preparing a polymeric transport system, comprising a) reacting a compound of formula:

(IXb1)

wherein J is

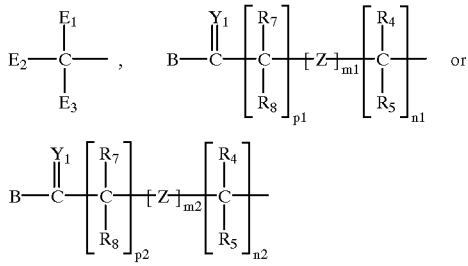

$E_{1-4}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy,

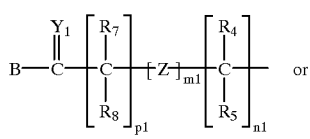 or

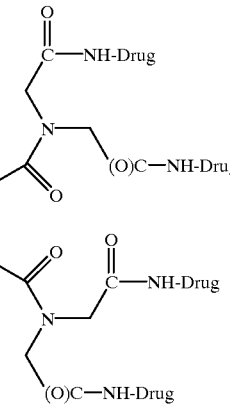

and at least one of $E_{1-4}$ includes a B moiety, wherein B is a leaving group, OH or

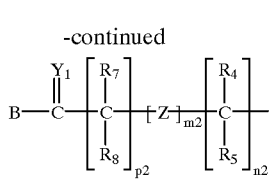

wherein $J_1$ is the same as J, or another member of the group defining J and $E_5$ is the same as $E_{1-4}$ or another member of the group defining $E_{1-4}$;

$Y_1$ is O, S, or $NR_9$;

$R_{4-5}$ and $R_{7-9}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted alkyls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

(m1) and (m2) are independently zero or one;

(n1), (n2), (p1), and (p2) are independently zero or a positive integer; and (Z) is an electron withdrawing group; with a compound of the formula:

(X)

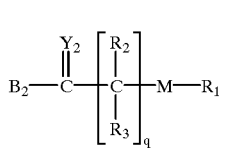

wherein $B_2$ is a leaving group which is capable of reacting with an unprotected amine;

$Y_2$ is O, S, or $NR_9$;

q is independently zero or a positive integer;

$R_{2-3}$ are selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

M is a heteroatom selected from either X or Q; wherein X is an electron withdrawing group and Q is a moiety containing a free electron pair positioned three to six atoms from $C(=Y_2)$; and ($R_1$) is a polymeric residue; and b) reacting the resultant compound with a sufficient amount of a biologically active moiety having a substitutable hydroxyl or amino group.

18. A method of preparing a polymeric transport system, comprising a) reacting a sufficient amount of a biologically active moiety having a substitutable hydroxyl or amino group with a compound of the formula:

 (IX)

wherein $B_3$ is a cleavable protecting group;

J is: 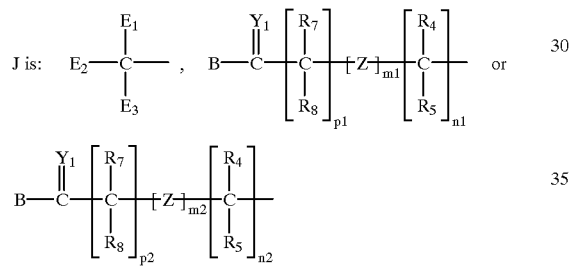

$E_{1-4}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy,

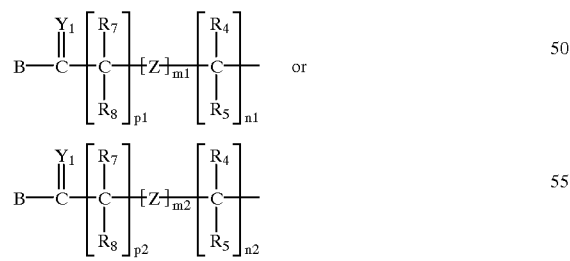

and at least one of $E_{1-4}$ includes a B moiety, wherein B is a leaving group, OH, or

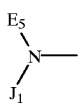

wherein $J_1$ is the same as J, or another member of the group defining J and $E_5$ is the same as $E_{1-4}$ or another member of the group defining $E_{1-4}$;

$Y_1$ is O, S, or $NR_9$;

$R_{4-5}$ and $R_{7-9}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

(m1) and (m2) are independently zero or one, (n1), (n2), (p1), and (p2) are independently zero or a positive integer; and (Z) is an electron withdrawing group; with a biologically active moiety having a hydroxyl or amine group;

b) deprotecting the resultant intermediate by removing $B_3$; and c) reacting the deprotected intermediate compound with a compound of the formula

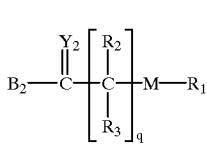 (X)

wherein $B_2$ is a leaving group which is capable of reacting with an unprotected amine;

$Y_2$ is O, S, or $NR_9$;

q is independently zero or a positive integer;

$R_{2-3}$ are selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

M is a heteroatom selected from either X or Q; wherein X is an electron withdrawing group and Q is a moiety containing a free electron pair positioned three to six atoms from $C(=Y_2)$; and ($R_1$) is a polymeric residue.

19. A method of treating a mammal with prodrugs, comprising:

administering to a mammal in need of such treatment an effective amount of a composition of claim 1 wherein B is a residue of a biologically active moiety.

* * * * *

UNITED STATES PATENT AND TRADEMARK OFFICE
CERTIFICATE OF CORRECTION

PATENT NO. : 6,395,266 B1
DATED : May 28, 2002
INVENTOR(S) : Martinez et al.

It is certified that error appears in the above-identified patent and that said Letters Patent is hereby corrected as shown below:

Column 31,
Line 15, after "$C_{3-12}$ branched alkyls" change "." to -- , --;
Line 17, after "$C_{1-6}$" delete ",";
Line 52, change "$Cl_{1-6}$" to -- $C_{1-6}$ --;
Line 53, after "$C_{1-6}$" delete "-";

Column 32,
Line 1, change "aralkyl.," to -- aralkyls, --.

Signed and Sealed this

Seventh Day of October, 2003

JAMES E. ROGAN
*Director of the United States Patent and Trademark Office*